(12) United States Patent
Lenges et al.

(10) Patent No.: US 8,030,513 B2
(45) Date of Patent: *Oct. 4, 2011

(54) RHEOLOGY CONTROL AGENTS

(75) Inventors: Christian Peter Lenges, Wilmington, DE (US); Yanhui Niu, Newark, DE (US); Yu-Ling Hsiao, Villanova, PA (US); Jiang Ding, Wilmington, DE (US); Robert John Barsotti, Franklinville, NJ (US); Renee J. Kelly, Media, PA (US); Robert James Butera, Havertown, PA (US); Young H. Kim, Hockessin, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/758,864

(22) Filed: Apr. 13, 2010

(65) Prior Publication Data

US 2010/0204376 A1  Aug. 12, 2010

(51) Int. Cl.
C07C 271/20 (2006.01)
C07C 271/22 (2006.01)
C07C 271/24 (2006.01)

(52) U.S. Cl. ........................ 560/115; 560/159
(58) Field of Classification Search .................. None
See application file for complete search history.

(56) References Cited

U.S. PATENT DOCUMENTS

| | | | |
|---|---|---|---|
| 3,585,160 A | 6/1971 | Miller et al. |
| 3,893,956 A | 7/1975 | Beres et al. |
| 4,242,243 A | 12/1980 | Antonelli et al. |
| 4,311,622 A | 1/1982 | Buter |
| 4,314,924 A | 2/1982 | Haubennestel et al. |
| RE31,309 E | 7/1983 | Antonelli et al. |
| 4,508,880 A | 4/1985 | Webster |
| 4,659,780 A | 4/1987 | Stamegna et al. |
| 4,677,028 A | 6/1987 | Heeringa et al. |
| 4,692,481 A | 9/1987 | Kelly |
| 4,851,294 A | 7/1989 | Buter et al. |
| 5,763,528 A | 6/1998 | Barsotti et al. |
| 5,866,259 A | 2/1999 | Harris et al. |
| 6,204,319 B1 | 3/2001 | Houze et al. |
| 6,221,484 B1 | 4/2001 | Leiter |
| 6,271,340 B1 | 8/2001 | Anderson et al. |
| 6,420,466 B1 | 7/2002 | Haubennestel et al. |
| 6,451,950 B1 | 9/2002 | Ma |
| 6,462,125 B1 | 10/2002 | White et al. |
| 6,462,144 B1 | 10/2002 | Ramesh et al. |
| 6,472,463 B1 | 10/2002 | Ma |
| 6,617,468 B2 | 9/2003 | Haubennestel et al. |
| 2002/0159961 A1 | 10/2002 | Yamato et al. |
| 2003/0005088 A1 | 1/2003 | Remer |

FOREIGN PATENT DOCUMENTS

| | | |
|---|---|---|
| EP | 0 683 214 | 11/1995 |
| EP | 1 162 242 | 12/2001 |
| WO | WO 02/064684 | 8/2002 |
| WO | WO 03/037849 | 8/2003 |
| WO | WO 03/070843 | 8/2003 |

*Primary Examiner* — Peter O Sullivan

(57) ABSTRACT

The present invention provides for a rheology control agent that includes a following compound represented by the following formula:

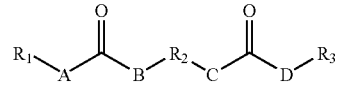

wherein A, B, C and D equal $CH_2$, CHR, NH, or O, and A, B, C and D may be the same or different and at least one of A and B equals NH and at least one of C and D equals NH; and wherein $R_1$, $R_2$, and $R_3$ may be the same or different and represent a linear, branched, hyper-branched, or dendritic ether, polyether or hydrocarbon based chain, optionally forming at least one carbon-based ring, being saturated or unsaturated and $R_2$ represents linear or branched alkylenes, ethers, polyethers, or polyester linkages and at least one of $R_1$, $R_2$, and $R_3$ comprises an ester group or an amide group which is branched off from the main chain; excluded from Formula (1) is a compound wherein $R_2$ is $CH_2$—$CH_2$—$CH_2$—$CH_2$—CH $(C(O)OCH_3)$, A, B, C, and D are equal to NH and $R_1$ and $R_3$ are both equal to a linear octyl hydrocarbon chain; the rheology control agent is suitable for solvent-borne and water-borne coating composition having improved rheology control useful for OEM refinishing or repainting the exterior of automobile and truck bodies and parts thereof.

5 Claims, No Drawings

RHEOLOGY CONTROL AGENTS

PRIORITY

This application claims priority from U.S. patent application Ser. No. 11/330,436, filed Jan. 12, 2006 and from Provisional U.S. Patent Application Ser. No. 60/643,482, filed Jan. 13, 2005, incorporated herein by reference.

BACKGROUND OF THE INVENTION

This invention relates to rheology control agents for coating compositions useful for finishing the exterior of automobiles and trucks, and in particular to liquid solvent-borne coating compositions containing rheology control agents that provide the composition with improved rheology control to facilitate a spray application that provides a high quality automotive finish.

DESCRIPTION OF THE PRIOR ART

The finish of choice currently being used on automobiles and trucks is a clear coat/color coat finish in which a clear coating is applied over the pigmented color coat or base coat to provide protection to the color coat and improve the appearance of the overall finish particularly, gloss and DOI (distinctness of image). Mono-coats of pigmented finishes are also used without a clear coat on some automobiles and trucks, in particular, older models. Primers, primer-surfacers, and sealers for many automotive and truck applications are applied initially before one of the aforementioned top coats are applied. All of the above compositions when applied by conventional spraying techniques, have rheology control problems, such as, running and sagging after application. Top coat finishes containing flake pigments or special effect pigments have problems with flake control and proper flake orientation for optimum appearance.

Additional problems are caused by many localities having regulations requiring the use of low VOC (volatile organic content) coating compositions to reduce air pollution. Typically, these low VOC coating compositions have a VOC of 2.1 pounds/gallon (252 g/l) or less and when applied by conventional spray techniques often have problems with running and sagging of the finish after application and also problems with proper flake orientation and control.

These low VOC coating compositions typically are used for OEM, refinishing or repainting of automobiles and trucks or parts thereof and are usually formulated using relatively low molecular weight polymers. However, as pointed out above, such compositions generally have poor rheology control and run and sag after spray application particularly when applied to vertical surfaces, such as, door panels and body side panels and have poor flake orientation and flake control. A rheology control agent is needed to form a coating composition having improved rheology control that prevent runs and sags after application and in general provides a finish with an acceptable appearance with good gloss and DOI.

Rheology control is also very critical for the low solids lacquer basecoats typically used in the refinishing or repainting of automobiles and trucks. These lacquer basecoats are typically applied at very low solids, as low as 10% by volume, using spray application. To achieve adequate hiding in these coatings, a dry film thickness of around 15 to 65 microns is typically required. Because of the very low volume solids of these coatings, the applied wet film thickness of these coatings can be around 350 microns or more. This requires the use of a very effective rheology control agent to prevent sagging and to give good flake orientation. Another aspect of these lacquer coatings is that they typically contain higher molecular weight binder components which can be incompatible with many conventional rheology control agents.

Rheology control agents are shown in U.S. Pat. No. 3,893,956, U.S. Pat. No. 4,311,622, U.S. Pat. No. 4,314,924, U.S. Pat. No. 4,677,028, U.S. Pat. No. 4,851,294, U.S. Pat. No. 6,420,466 B1, U.S. Pat. No. 6,617,468 B2, and EP 0683214, EP 1162242, DE 10241853 B3 and WO 2003/037849. These rheology control agents of the prior art in general cannot be formulated into high solids compositions and do not provide the necessary level of optical clarity to the resulting finishes and form finishes having low DOI levels, particularly when the coating compositions are ambient temperature curing compositions. Some of these rheology control agents have to be prepared in the presence of the binder of the coating composition to achieve the desired level of rheology control, which adds to the manufacturing costs of the composition by requiring additional manufacturing steps and the use of specific and also expensive equipment. Some rheology control agents, for example, taught by U.S. Pat. No. 6,617,468 B2 limit the weatherability of the resulting finish, which over time negatively impacts the appearance of the finish. Some rheology control agents, for example, taught by U.S. Pat. No. 4,311,622 are limited in their compatibility with the resin system. These rheology control agents are based on a symmetrical structure. Furthermore, some rheology control agents, for example, taught by U.S. Pat. No. 4,311,622 or WO 2002/064684 show insufficient compatibility in the resin system of choice especially rheology control agents prepared using hydroxyl functional monoamines.

U.S. Patent Publication 2002/0159961, published Oct. 31, 2002 shows gelling agents that are used to gel oils and in cosmetic compositions, such as, antiperspirants but have not been suggested for use in coating compositions.

Accordingly, there is still a need for rheology control agents for coating compositions for a wide variety of applications that will provide an acceptable level of rheology control on application of the coating composition without deteriorating the appearance, durability or weatherability of both high solids and low solids coating compositions that are often used in OEM automotive and truck manufacturing and to refinish or repaint automobile and truck bodies or parts thereof.

SUMMARY OF THE INVENTION

The present invention is directed towards rheology control agents used in both low and high solids solvent-borne coating compositions and water-borne coating compositions useful for OEM and refinishing or repainting the exterior of automobile and truck bodies and parts thereof, such coating compositions comprising a liquid carrier, a film forming binder and a rheology control agent. The rheology control agent of this invention used in the coating composition comprises the following compound represented by the following formula including isomers and mixtures of isomers thereof:

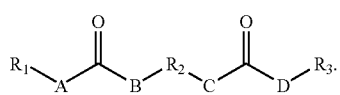

Formula (I)

wherein A, B, C and D equal $CH_2$, CHR, NH, or O, and A, B, C and D may be the same or different and at least one of A and B equals NH and at least one of C and D equals NH; and wherein $R_1$, $R_2$, and $R_3$ may be the same or different and represent a linear, branched, hyper-branched, or dendritic ether, polyether or hydrocarbon based chain, optionally forming at least one carbon-based ring, being saturated or unsaturated and $R_2$ represents linear or branched alkylenes, ethers, polyethers, or polyester linkages and at least one of $R_1$, $R_2$, and $R_3$ comprises an ester group which is branched off from the main chain; excluded from Formula (I) is a compound wherein $R_2$ is $CH_2$—$CH_2$—$CH_2$—$CH_2$—$CH(C(O)OCH_3)$, A, B, C, and D are equal to NH and $R_1$ and $R_3$ are both equal to a linear octyl hydrocarbon chain.

DETAILED DESCRIPTION OF THE INVENTION

The features and advantages of the present invention will be more readily understood, by those of ordinary skill in the art, from reading the following detailed description. It is to be appreciated those certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

All patents, patent applications and publications referred to herein are incorporated by reference in their entirety.

The rheology control agents of this invention are useful in solvent-borne coating compositions and water-borne coating compositions and in particular are useful in clear and pigmented paint compositions used for OEM, refinishing or repainting the exterior of automobiles and trucks. The rheology control agent improves and controls the rheology of the coating compositions to facilitate spray applications and provide a Class A automotive finish having an excellent overall appearance and good DOI. The resulting finish does not sag or run particularly when spray applied to vertical surfaces. Under high shear conditions such as occur when the coating composition is applied, for example, by spraying, the viscosity of the composition is significantly reduced. After the coating is applied, the shear conditions are low and the viscosity increases significantly to eliminate runs and sags on a vertical surface and provides a finish with an excellent appearance. Also, proper orientation of flake or special effects pigments that are used in base coats and mono-coats is controlled and the pigment and flake settling properties of such coatings are also improved. The rheology control agents of this invention can also be used in primers, primer surfacers, and primer fillers.

The rheology control agent must be compatible with the coating composition and not deteriorate the properties of the resulting finish, such as, gloss and DOI or the weatherability or durability of the finish. Small changes in the chemical composition of a compound can significantly affect its use as a rheology control agent. Rheological measurements are useful in characterizing the effectiveness of a rheology control agent, but the final measure of the ability of a compound to provide effective rheology control in a coating composition, is to test the compound in a coating composition using conventional application conditions, such as, spray application, optionally, with subsequent drying or baking of the resulting finish and observe the resulting appearance of the finish.

Typically, solvent-borne coating compositions or waterborne coating compositions containing the novel rheology control agent comprise 5 to 95 percent by weight of a liquid carrier, based on the weight of the coating composition, and 5 to 95 percent by weight of binder, which includes the rheology control agent, also based on the weight of the coating composition. Typically, the level of rheology control agent in such coating compositions is in the range of 0.1 to 30 percent by weight, based on the weight of the binder, and preferably, 0.1 to 10 percent by weight based on the weight of the binder.

Coating compositions can be 100% binder solids compositions and the rheology control agents are used in the ranges shown above.

The term "binder" as used herein refers to the film forming constituents of the composition and includes any crosslinking components, such as, polyisocyanates, optional polymeric and/or oligomeric components, and optional reactive diluents. Solvents, pigments, catalysts, antioxidants, U.V. absorbers, light stabilizers, leveling agents, antifoaming agents, anti-cratering agents, adhesion promoting agents are not included in the term.

Molecular weight (both number and weight average) is determined by gel permeation chromatography utilizing a high performance liquid chromatograph supplied by Hewlett-Packard, Palo Alto, Calif. and unless otherwise stated the liquid phase used was tetrahydrofuran and the standard was polymethylmethacrylate or polystyrene.

"Tg" (glass transition temperature) is in ° C. and determined by Differential Scanning Calorimetry or calculated according to the Fox Equation.

"Lacquer" is a coating composition, which dries via solvent evaporation without any substantial crosslinking of the binder of the coating composition.

The novel rheology control agent of this invention used coating composition is a compound having following formula

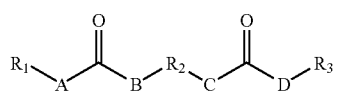

Formula (I)

wherein A, B, C and D equal $CH_2$, CHR, NH, or O, and A, B, C and D may be the same or different and at least one of A and B equals NH and at least one of C and D equals NH; and wherein $R_1$, $R_2$, and $R_3$ may be the same or different and represent a linear, branched, hyper-branched, or dendritic ether, polyether or hydrocarbon based chain, optionally forming at least one carbon-based ring, being saturated or unsaturated and $R_2$ represents linear or branched alkylenes, ethers, polyethers, or polyester linkages and at least one of $R_1$, $R_2$, and $R_3$ comprises an ester group which is branched off from the main chain; excluded from Formula (1) is a compound wherein $R_2$ is $CH_2$—$CH_2$—$CH_2$—$CH_2$—$CH(C(O)OCH_3)$, A, B, C, and D are equal to NH and $R_1$ and $R_3$ are both equal to a linear octyl hydrocarbon chain.

The following formulas illustrate particularly useful rheology control agents used in solvent-borne coating compositions, water-borne coating, compositions or 100% solids coating compositions and provide the compositions with excellent rheology control on application and form finishes that have excellent overall appearance, good DOI, do not sag or run on application, and have good flake orientation. Further, these rheology control agents can be used in conjunction with a wide variety of coating compositions containing as the binder, polyacrylates, linear poly(meth)acrylates, branched, grafted or segmented poly(meth) acrylates, acrylic alkyd resins, polyesters, branched copolyesters, carbamates, oligomers, or polyesterurethanes. These coating compositions may also utilize crosslinking agents, such as, polyisocyanates, alkylated melamines, melamine derivatives, and epoxides and other crosslinking agents.

In one embodiment of the above Formula I, A, B, C and D are NH and $R_2$ comprises an ester group which is branched off from the main chain of the molecule. Specific examples of this embodiment include, but are not limited to the following structures:

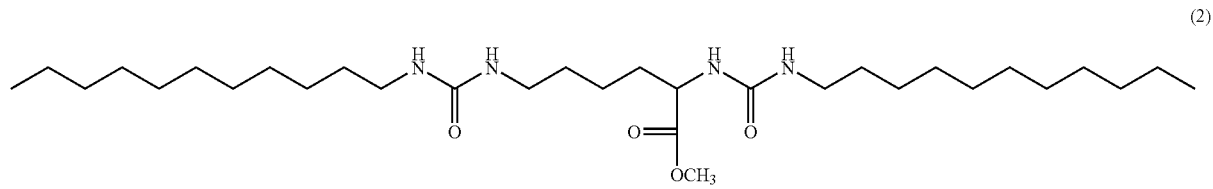

(2)

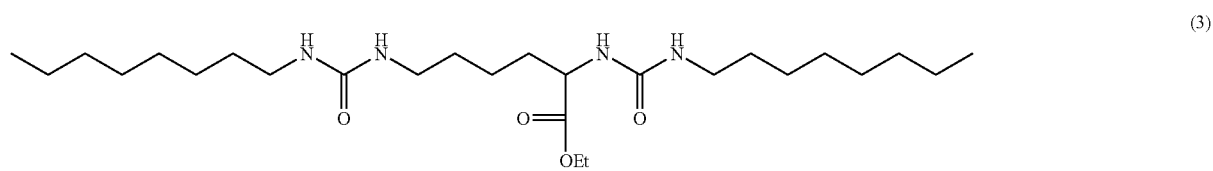

(3)

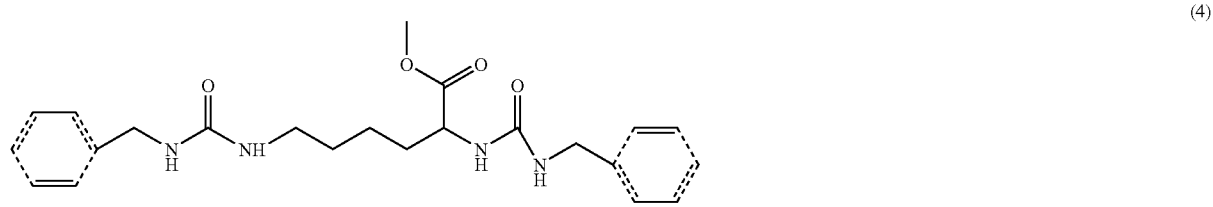

(4)

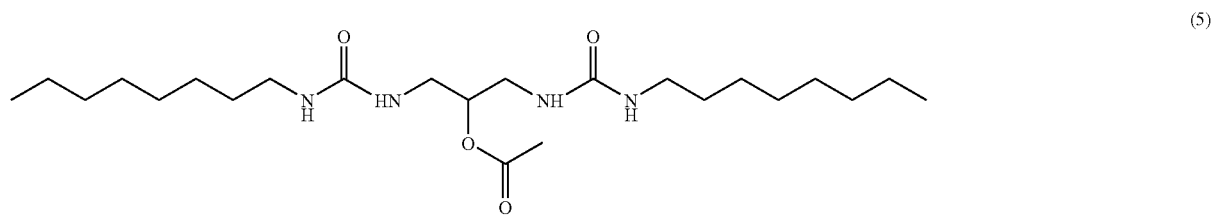

(5)

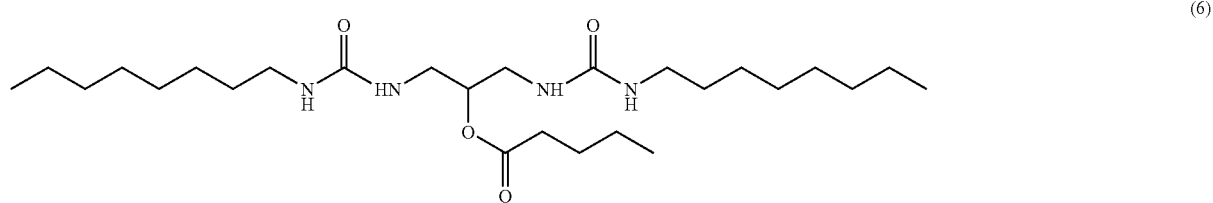

(6)

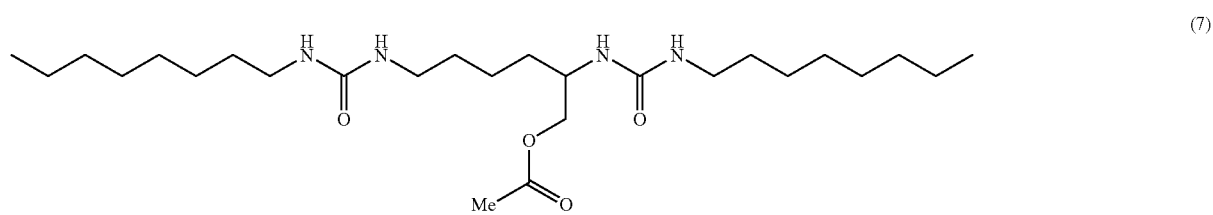

(7)

-continued
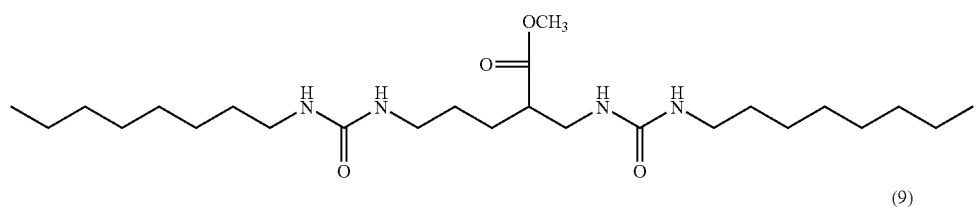
(8)
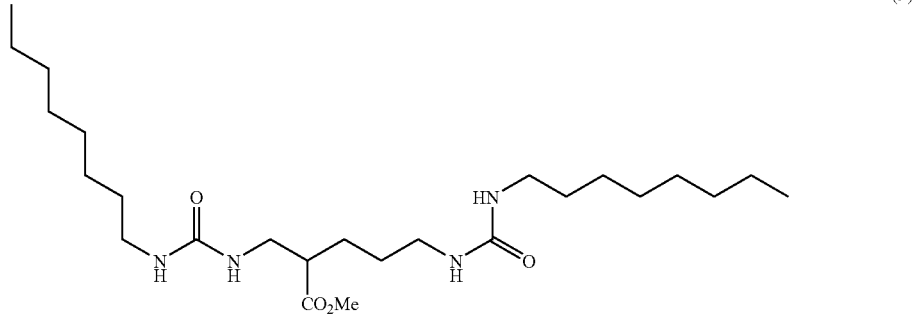
(9)
(10)
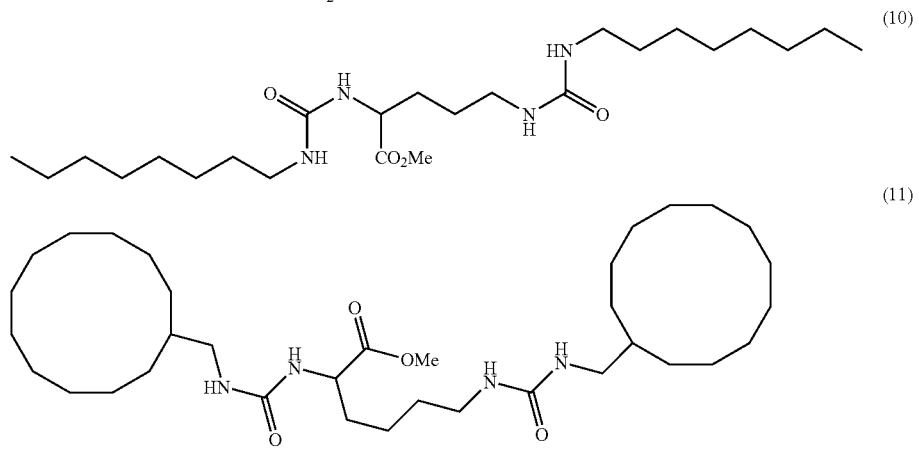
(11)
In a second embodiment of the above Formula I, A, B, C and D are NH, $R_2$ comprises an ester group which is branched off from the main chain of the molecule, and $R_1$ and $R_3$ each comprises at least one ester group. Specific examples of this embodiment include, but are not limited to the following structures:
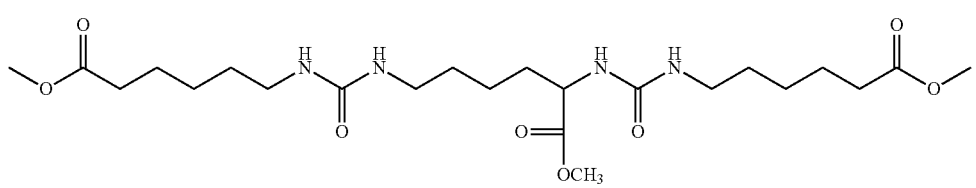
(12)
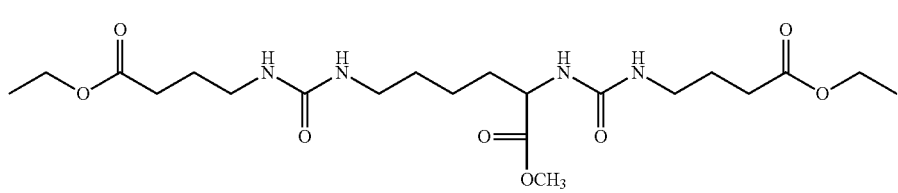
(13)

(14)
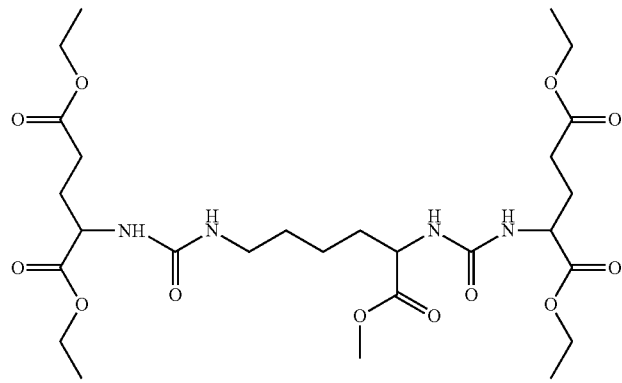
(15)
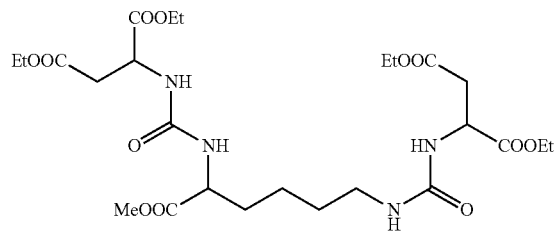
(16)
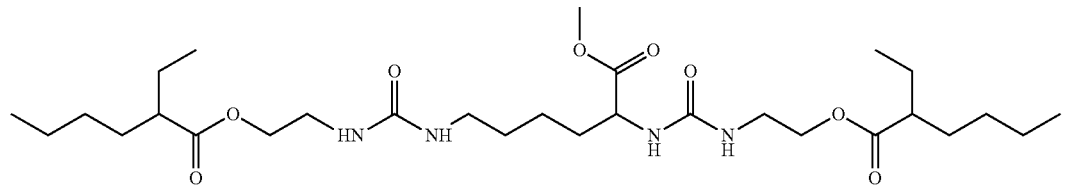
In a third embodiment of the above Formula I, A, B, C and D are NH and $R_2$ comprises an ester group which is branched off from the main chain of the molecule, and $R_1$ and $R_3$ each comprises at least one urethane group. Specific examples of this embodiment include, but are not limited to the following structures:
(17)
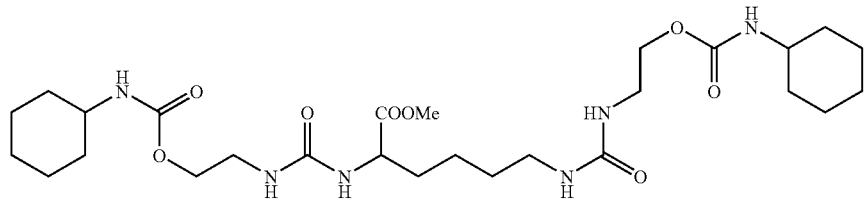
(18)
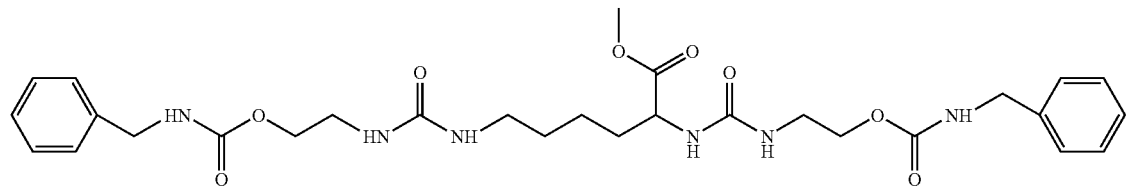
(19)
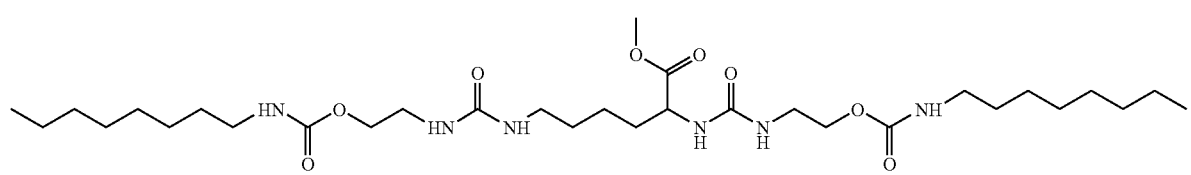

In yet another embodiment of the above Formula I wherein A and D are O and B and C are NH and R$_2$ comprises and ester group which is branched off from the main chain of the molecule. Specific examples of this embodiment include, but are not limited to the following structures:

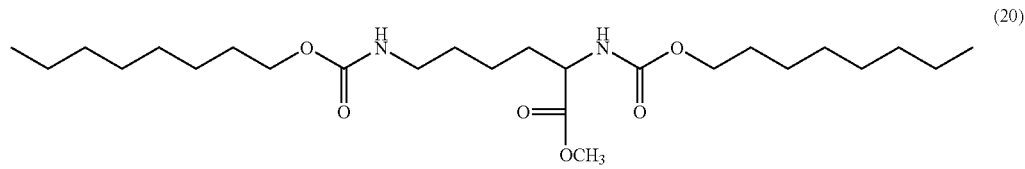

(20)

In another embodiment of the above Formula I wherein A and D are O and B and C are NH, R$_2$ comprises an ester group which is branched off from the main chain of the molecule, and R$_1$ and R$_3$ comprise at least one urea group. Specific examples of this embodiment include, but are not limited to the following structures

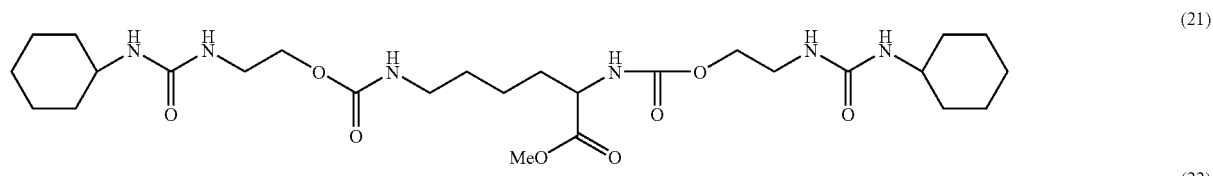

(21)

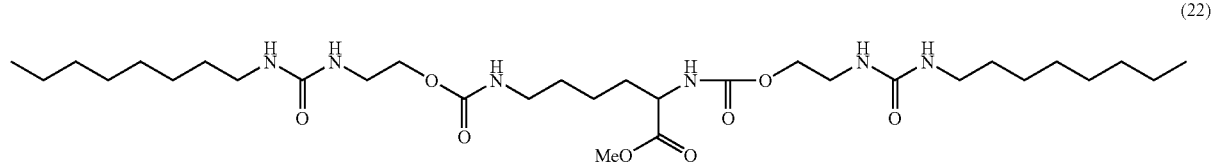

(22)

In another embodiment of the above Formula I wherein A, B, C, and D are NH and R$_1$ and R$_3$ each comprise at least one ester group which is branched off the main chain. Specific examples of this embodiment include, but are not limited to the following structures

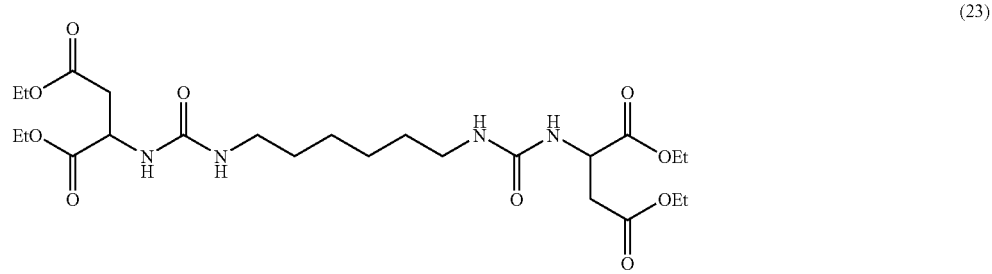

(23)

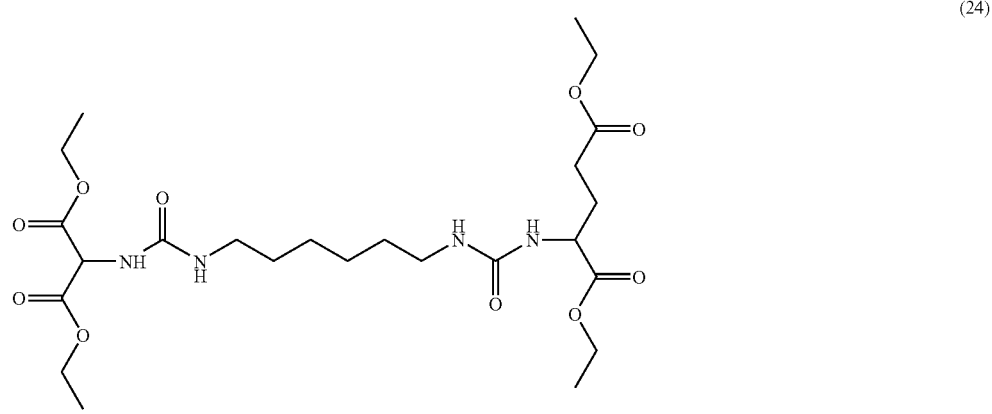

(24)

-continued
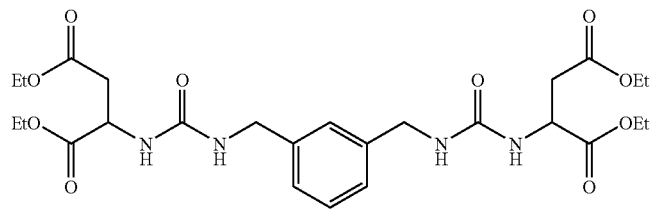
(25)
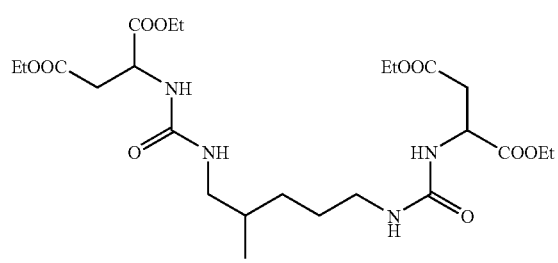
(26)
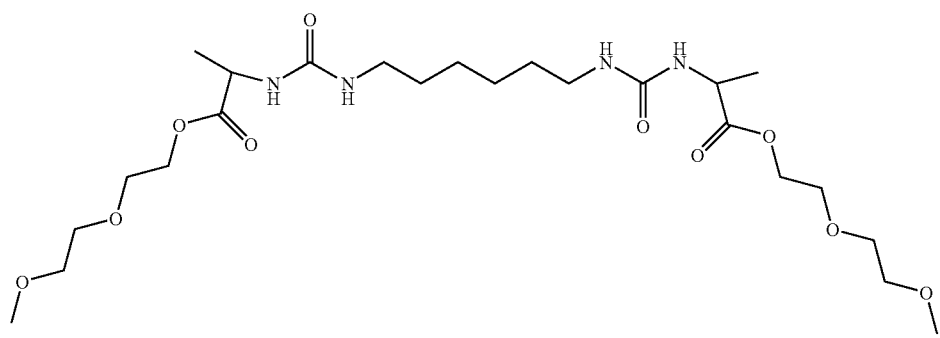
(27)
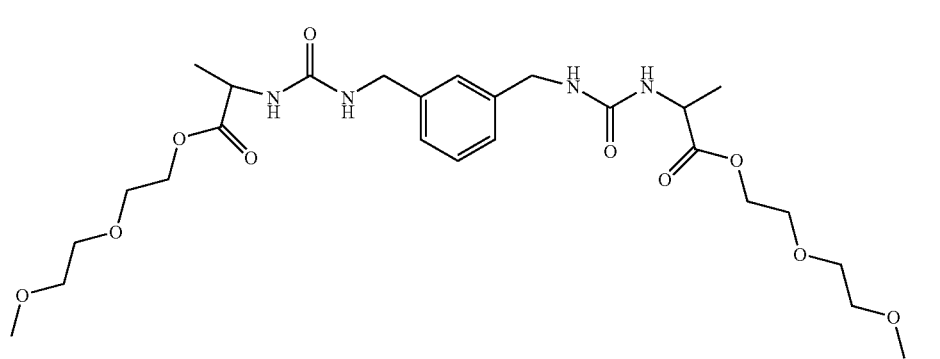
(28)
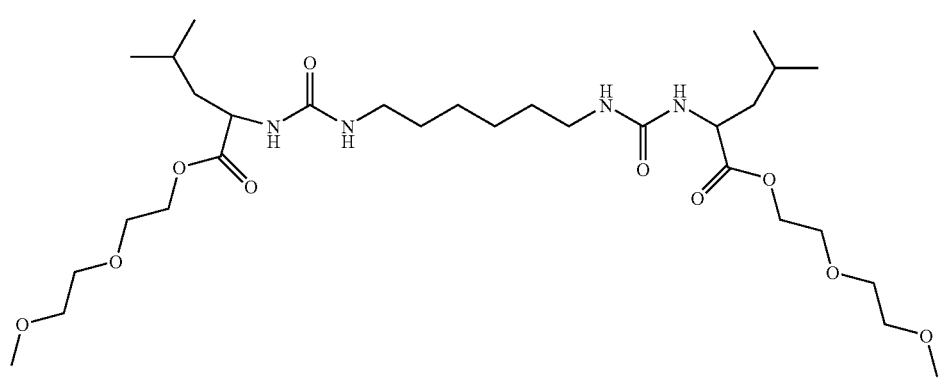
(29)

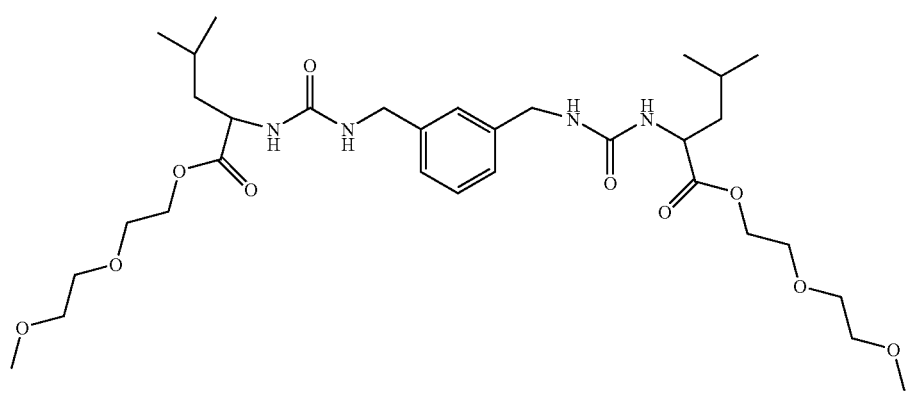

(30)

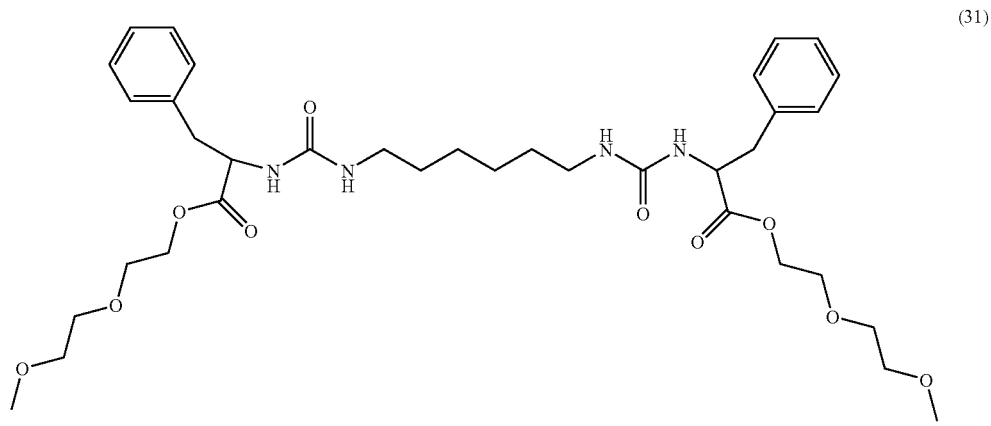

(31)

In an embodiment of the above Formula I wherein A, C, and D are NH, B is O, R$_2$ comprises at least one ester group which is branched off the main chain. Specific examples of this embodiment include, but are not limited to the following structures

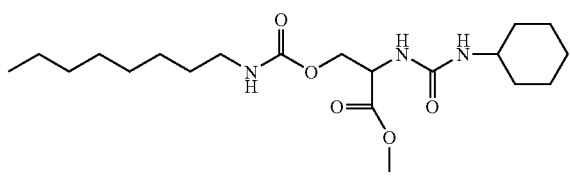

(32)

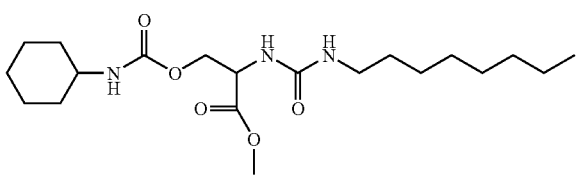

(33)

In an embodiment of the above Formula I, wherein A and D are O, and B and C are NH, and R$_1$ and R$_3$ each comprises at least one urea group and one ester group which is branched off from the main chain of the molecule. Specific examples of this embodiment include, but are not limited to the following structures:

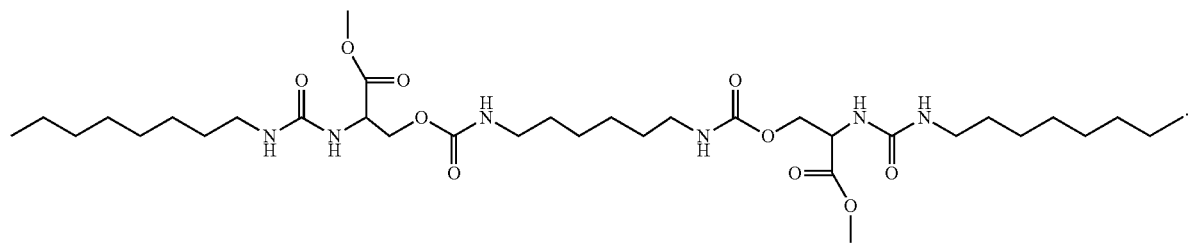

(34)

The rheology control agents shown in Formulas 2 to 34 are novel compounds.

The branched rheology control agents of this invention may be formed using a variety of synthetic methods. Synthesis of structures (2-16, 23-31) for example, may comprise reacting an amine with a diisocyanate in a suitable reaction vessel generally at a temperature between 0° C. and 120° C., preferably, from 10° C. to 80° C. and optionally, in the presence of a diluent.

For example, the synthesis of the branched rheology control agent of this invention comprises adding a solution of an organic diisocyanate in a dry solvent, such as chloroform, under an inert atmosphere, such as nitrogen, to a solution of a corresponding amino acid ester typically in a 1:2 molar ratio. The resulting reaction mixture is held under relatively cold conditions, such as 10° C., and then after addition of the diisocyanate solution the reaction mixture is allowed to warm and the reaction to continue, for example, about 1-3 hours with agitation or until the IR (infra red) isocyanate peak (about 2258 cm$^{-1}$) disappears as monitored by an IR spectrophotometer. At the completion of the reaction, the rheology control agent that was farmed is isolated, for example, by conventional techniques, like filtration or evaporation of solvent and the agent is washed with appropriate solvent and dried, for example, in a vacuum at room temperature.

Alternatively, structures 2-16 and 23-31 may be obtained by reacting an isocyanate with a diamine in a suitable reaction vessel, generally at a temperature between 0° C. and 120° C., preferably, from 10° C. to 80° C. and optionally, in the presence of a diluent.

Suitable amines or diamines for the formation of subject invention include, but are not limited to, 2-amino-4-methylpentanoate alkyl ester, aminoethanoate alkyl ester, 2-amino-3-phenylpropanoate alkyl ester, 2-aminopropanoate alkyl ester, 2-amino-3-carbamoylpropanoate alkyl ester, diethyl 2-aminobutanedioate alkyl ester, 2-amino-4-carbamoylbutanoate alkyl ester, 2-aminopentanedioate alkyl ester, 2-amino-3-methylpentanoate alkyl ester, 2-amino-4-(methylthio)butanoate ester, 2-amino-3-hydroxypropanoate alkyl ester, 2-amino-3-hydroxybutanoate alkyl ester, 2-amino-3-(4-hydroxyphenyl)-propanoate alkyl ester, 2-amino-3-methylbutanoate alkyl ester, 2,6-diaminohexanoate alkyl ester, di(ethylene glycol) methyl ether 2-amino-4-methylpentanoate ester, di(ethylene glycol) methyl ether aminoethanoate ester, di(ethylene glycol) methyl ether 2-amino-3-phenylpropanoate, ethyl 2-aminobutanedioate, 2-amino-2-(hydroxyethyl)propane-1,3-diol, 1,3-diamino-2-hydroxypropane, butyl amine, octyl amine, hexyl amine, decyl amine, undecyl amine, dodecyl amine, cyclohexyl amine, cyclododecylamine, methyl 1,5-diamino-2-panetanoate, methyl 6-aminocaproate, ethyl 4-aminobutyrate, hexamethylene diamine, cyclohexyl diamine, xylylene diamine, polyoxyalkylene monoamines (Jeffamine® M), polyoxyalkylene diamines (Jeffamine® D), tetramethylene diamine, nobornene diamine, L-ornithine methyl ester, L-lysine ethyl ester, L-lysine butyl ester, 3-amino-alanine ethyl ester or mixtures thereof. The alkyl groups in the aforementioned section refer to methyl, ethyl, propyl, butyl, isoproyl, and isobutyl groups.

Suitable isocyanates or diisocyanates for the formation of subject invention include, but are not limited to, hexamethylene diisocyanate, 1,4-diisocyanatobutane, toluene 2,4-diisocyanate, toluene 2,6-diisocyanate, 4,4'-diphenyl methane diisocyanate, 2,2'-diphenyl methane diisocyanate, 2,4'-diphenyl methane diisocyanate, isophorone diisocyanate, m-tetramethylxylene diisocyanate, dicyclohexylmethane 4,4'-diisocyanate, naphthalene 1,5-diisocyanate, p-phenylene diisocynate, methyl 2,6-diisocyanatohexanoate, octyl isocyanate, cyclohexyl isocyanate, butyl isocyanate, hexyl isocyanate, decyl isocyanate, undecyl isocyanate, or mixtures thereof.

The synthesis of branched rheology control agents (17, 18, 19, 21, and 22) of this invention may be formally separated into several steps. These steps may be carried out sequentially in one reaction vessel or in different reaction vessels followed by separation and/or purification steps. Certain rheology control agents (21 and 22) of this invention may be formed by first reacting an amino alcohol component with a mono-isocyanate component. This intermediate is further reacted with a diisocyanate component to form the rheology control agent. The other rheology control agents (17, 18 and 19) are formed by first reacting an amino alcohol component with a diisocyanate component. The reaction temperature and reactant concentration is selected to favor the formation of the intermediate addition product. Further reaction with a mono-isocyanate component then forms the rheology control agent of this invention.

Suitable aminoalcohols for the formation of subject invention include but are not limited to 2-amino-2-(hydroxyethyl)propane-1,3-diol, 1,3-diamino-2-hydroxypropane, 2-hydroxyethylamine, 3-hydroxypropylamine, or mixtures thereof.

Suitable mono-isocyanates or disocyanates for the formation of subject invention include but are not limited to, methyl 2,6-diisocyanatohexanoate, octyl isocyanate, cyclohexyl isocyanate, butyl isocyanate, hexyl isocyanate, undecyle isocyanate, or mixtures thereof.

The branched rheology control agents of this invention may be formed using a variety of synthetic methods. Synthesis of structure (20) for example may comprise reacting a diisocyanate with an alcohol in the presence of a urethane catalyst such as dibutyl tin dilaurate at temperature from 25° C. to 120° C., preferably from 40° C. to 90° C.

Suitable diisocyanates include but are not limited to methyl 2,6-diisocyanatohexanoate.

Suitable alcohol include but are not limited to butanol, hexanol, octanol, decyl alcohol, undecyl alcohol, monomethyl ether polyethylene glycol, and mixtures thereof.

The synthesis of branched rheology control agents (32 & 33) of this invention may be formally separated into several steps. These steps may be carried out sequentially in one reaction vessel or in different reaction vessels followed by separation and/or purification steps. Certain rheology control agents (32 & 33) of this invention may be formed by first reacting an amino acid ester with a mono-isocyanate component at 1:1 molar ratio in a dry solvent. This intermediate is further reacted with another or the same monoisocyanate component to form the rheology control agent.

Suitable amino acid ester for the formation of subject invention include but are not limited to 3-hydroxy-aspartic acid dimethyl ester, serine benzylester, serine t-butylester, serine ethylester, serine methylester, serine isopropyl ester, β-hydroxy-phenylalanine methyl ester, threonine methyl ester, or mixtures thereof.

Suitable mono-isocyanates for the formation of subject invention include but are not limited to, octyl isocyanate, cyclohexyl isocyanate, butyl isocyanate, hexyl isocyanate, undecyle isocyanate, decyle isocyanate, or mixtures thereof.

Suitable diisocyanates for the formation of subject invention include, but are not limited to, hexamethylene diisocyanate, 1,4-diisocyanatobutane, toluene 2,4-diisocyanate, toluene 2,6-diisocyanate, 4,4'-diphenyl methane diisocyanate, 2,2'-diphenyl methane diisocyanate, 2,4'-diphenyl methane diisocyanate, isophorone diisocyanate, m-tetramethylxylene diisocyanate, dicyclohexylmethane 4,4'-diisocyanate, naphthalene 1,5-diisocyanate, p-phenylene diisocynate, methyl 2,6-diisocyanatohexanoate, or mixtures thereof.

The synthesis of branched rheology control agents (34) of this invention may be formally separated into several steps. These steps may be carried out sequentially in one reaction vessel or in different reaction vessels followed by separation and/or purification steps. Certain rheology control agents (34) of this invention may be formed by first reacting an amino acid ester with a mono-isocyanate component at 1:1 molar ratio in a dry solvent. This intermediate is further reacted with another diisocyanate component to form the rheology control agent at 2:1 molar ratio.

The rheology control agent can be formulated, dissolved, or dispersed in an organic solvent or a mixture of solvents. More preferably, the solvent is a ketone, ester, acetate, blend of ester and alcohol, aprotic amide, aprotic sulfoxide, organic acid with a pKa less than 5.5, blend of organic acids with the above solvents or aprotic amine. Examples of other useful solvents include methyl ethyl ketone, methyl isobutyl ketone, methyl amyl ketone, amyl acetate, ethylene glycol butyl ether acetate, propylene glycol monomethyl ether acetate, xylene, N-methylpyrrolidone, 1-ethyl-2-pyrrolidinone, 1-(2-hydroxyethyl)-2-pyrrolidinone, 1-cyclohexyl-2-pyrrolidone, 1-ethyl-2-pyrrolidinone, 1-vinyl-2-pyrrolidone, 2-pyrrolidone-5-carboxylic acid, 1,5-dimethyl-2-pyrrolidinone, 1-benzyl-2-pyrrolidinone, acetic acid, dodecylbenzene sulfonic acid, alkyl sulfonic acids, aryl sulfonic acids, formic acid, phosphoric acid, blends of acids and N-methylpyrrolidone, blends of butyl acetate and butanol, blends of aromatic hydrocarbons, or mixtures thereof.

The rheology control agent of this invention can be combined with the film forming coating system using a variety of methods. For example, the rheology control agent can be added to the film forming coating mixture as a solid in powder form. Agitation methods, known to those skilled in the art, may be used to disperse, dissolve or distribute the rheology control agent. The use of a high speed disperser has been found to be a particularly effective dispersing technique at dispersing these rheology control agents in a binder component and solvent of the coating formulation. This dispersion is subsequently added to the other components of the coating formulation to make the final coating. Alternatively, the rheology control agent can be prepared directly using the binder system of the film forming coating mixture as the reaction medium using the general synthesis procedures outlined above.

Conventional rheology control agents have been produced in the presence of a binder resin as shown, for example, in GB 1,454,414, wherein a urea adduct is prepared in situ in the presence of the binder. The rheology control agents of this invention may also be produced in the presence of a binder to directly form a desired fibril structure in the binder resin. The length of the fibrils can be adjusted as known to those skilled in the art using, for example, a shear treatment, or by modifying the mixing conditions.

The rheology control agents of this invention may also be prepared following the outlined synthesis procedures directly from the starting materials described above by using a nonsolvent, which has a limited solubility for the product. This strategy results in a precipitate that can be used as such, be milled in order to reduce the average length, or be re-crystallized, for example to increase the purity or to change the structural morphology or fibril length. In the preparation process of the rheology control agent the dosing conditions or the stirrer speed can be changed to influence the average structure build or fibril formation.

Alternatively, the rheology control agents of this invention may also be utilized in the form of their solutions at temperatures between 0 and 150° C. and in a polar solvent optionally containing 0-3.0 mols of an inorganic or organic acid compounds per urea group. The rheology control agents of this invention as defined above have a solids content of 10-75 wt. % and preferably of 15-40 wt. %. These solutions of the rheology control agent can be used as additives to a coating formulation. Suitable solvents for this purpose are, for example, N-methylpyrrolidone, dimethyl acetamide, n-butanol, aliphatic diols, butyl glycol, acetic acids, 1-ethyl-2-pyrrolidinone, 1-(2-hydroxyethyl)-2-pyrrolidinone, 1-cyclohexyl-2-pyrrolidone, 1-ethyl-2-pyrrolidinone, 1-vinyl-2-pyrrolidone, 2-pyrrolidone-5-carboxylic acid, 1,5-dimethyl-2-pyrrolidinone, 1-benzyl-2-pyrrolidinone and mixtures thereof.

Optionally, inorganic or organic acid compounds can be added to maximize the solids content and stability of these solutions. By stability is meant no significant precipitation or gelation upon aging either at room temperature or at elevated temperature (up to 50° C.) storage. Preferred inorganic compounds used in these solutions and are selected from LiCl, LiBr, NaCl, KCl, CaCl2, LiNO3, lithium acetate, lithium acetylacetonate, tetraalkylammonium phosphate, organophosphate, LiOC(O)Me or other Li-salts of carboxylic acids, sulfonic acids, benzoic acids or substituted benzoic acids, with LiCl as the preferred inorganic compound. Preferred organic acid compounds used in these solutions are selected from dodecylbenzene sulfonic acid in isopropanol, p-toluene sulfonic acids and trifluoromethane sulfonic acids. Surprisingly, it has been found that some of these rheology control agents can be dissolved at high solids (>10% by weight) in solvent without the use of these inorganic compounds or organic acids.

The solvent-borne coating compositions and water-borne coating compositions of this invention containing rheology control agents are useful in a wide variety of applications, such as, clear coating compositions, base coating compositions, pigmented mono coating compositions, primer surfacers and primer fillers. Typical binders used in these compositions are acrylic polymers, such as, poly(meth)acrylates, meaning both polyacrylates and polymethacrylates, linear, branched, grafted, or segmented poly(meth)acrylates, polyacrylourethanes, polyesters, branched copolyesters, oligomers, e.g. urethane oligomers, polyester urethanes, polyepoxides and carbamate functional polymers. Typical crosslinking agents that may be used in these compositions are polyisocyanates, blocked polyisocyanates, melamine crosslinking agents, alkylated melamines, silanes, benzoguanamines and other crosslinking agents known to those skilled in the art.

The acrylic polymers used to form coating compositions containing the novel rheology control agent of this invention may be random polymers or structured copolymers, such as, block or graft copolymers. Particularly useful structured copolymers are the branched acrylics with segmented arms as disclosed in U.S. Ser. No. 10/983,462 filed Nov. 8, 2004 and U.S. Ser. No. 10/983,875 filed Nov. 8, 2004, both of which are incorporated herein by reference.

A block copolymer used in the present invention may have an AB diblock structure, or ABA or ABC triblock structure, for example, Graft copolymers can be used in the present invention having a backbone segment and a side chain segment(s). Random copolymers that can be used have polymer segments randomly distributed in the polymer chain.

Acrylic AB, ABA or ABC block copolymers can be prepared by using a stepwise polymerization process such as anionic, group transfer polymerization (GTP) taught in U.S. Pat. No. 4,508,880, Webster et al., ""Living" polymers and process for their preparation", atom transfer radical polymerization (ATRP) taught in U.S. Pat. No. 6,462,125, White et al., and radical addition fragmentation transfer (RAFT) taught in U.S. Pat. No. 6,271,340, Anderson, et al. "Method of controlling polymer molecular weight and structure". Polymers so produced have precisely controlled molecular weight, block sizes and very narrow molecular weight distributions.

Aqueous coating compositions containing AB block copolymers as pigment dispersants disclosed in Houze et al. U.S. Pat. No. 6,204,319, which is hereby incorporated by reference, can utilize the novel rheology control agents of this invention.

Graft copolymers may be prepared by a macromonomer approach using the special cobalt chain transfer (SCT) method reported in U.S. Pat. No. 6,472,463, Ma, the disclosure of which is herein incorporated by reference.

Random copolymers can be prepared using conventional free radical polymerization techniques as described in U.S. Pat. No. 6,451,950, Ma. The disclosure of which is herein incorporated by reference.

Typically useful acrylic polymers have a number average molecular weight of about 1,000 to 100,000, a Tg of 10 to 100° C. and contain moieties, such as, hydroxyl, carboxyl, glycidyl and amino groups. Typically useful acrylic polymers are known in the art and the following are typical examples of monomers used to form such polymers: linear alkyl (meth) acrylates having 1 to 12 carbon atoms in the alkyl group, cyclic or branched alkyl(meth)acrylates having 3 to 12 carbon atoms in the alkyl group including isobornyl(meth)acrylate, hydroxy alkyl(meth)acrylates having 1 to 4 carbon atoms in the alkyl group, glycidyl(meth)acrylate, hydroxy amino alkyl (meth)acrylates having 1 to 4 carbon atoms in the alkyl group, and the polymers can contain styrene, alpha methyl styrene, vinyl toluene, (meth)acrylonitrile (meth)acryl amides, (meth) acrylic acid, (meaning both acrylic acid and methacrylic acid) trimethoxysilylpropyl (meth)acrylate and the like.

Examples of (meth)acrylic acid esters useful for forming these acrylic polymers are methyl acrylate, ethyl acrylate, isopropyl acrylate, tert.-butyl acrylate, n-butyl acrylate, isobutyl acrylate, 2-ethylhexyl acrylate, lauryl acrylate, stearyl acrylate and the corresponding methacrylates. Examples of (meth)acrylic acid esters with cyclic alcohols are cyclohexyl acrylate, trimethylcyclohexyl acrylate, 4-tert.-butylcyclohexyl acrylate, isobornyl acrylate and the corresponding methacrylates.

Additional unsaturated monomers that do not contain additional functional groups useful for forming the acrylic polymers are, for example, vinyl ethers, such as, isobutyl vinyl ether and vinyl esters, such as, vinyl acetate, vinyl propionate, vinyl aromatic hydrocarbons, preferably those with 8 to 9 carbon atoms per molecule. Examples of such monomers are styrene, alpha-methylstyrene, chlorostyrenes, 2,5-dimethylstyrene, p-methoxystyrene, vinyl toluene. Styrene is preferably used.

Small proportions of olefinically polyunsaturated monomers may also be used. These are monomers having at least 2 free-radically polymerizable double bonds per molecule. Examples of these are divinylbenzene, 1,4-butanediol diacrylate, 1,6-hexanediol diacrylate, neopentyl glycol dimethacrylate, glycerol dimethacrylate.

Hydroxy-functional (meth)acrylic polymers generally are formed by free-radical copolymerization using conventional processes well known to those skilled in the art, for example, bulk, solution or bead polymerization, in particular by free-radical solution polymerization using free-radical initiators.

Suitable hydroxyl-functional unsaturated monomers that are used to introduce hydroxyl groups into the acrylic polymer are, for example, hydroxyalkyl esters of alpha,beta-olefinically unsaturated monocarboxylic acids with primary or secondary hydroxyl groups. These may, for example, comprise the hydroxyalkyl esters of acrylic acid, methacrylic acid, crotonic acid and/or isocrotonic acid. The hydroxyalkyl esters of (meth)acrylic acid are preferred. Examples of suitable hydroxyalkyl esters of alpha,beta-olefinically unsaturated monocarboxylic acids with primary hydroxyl groups are hydroxyethyl(meth)acrylate, hydroxypropyl (meth)acrylate, hydroxybutyl(meth)acrylate, hydroxyamyl(meth)acrylate, hydroxyhexyl(meth)acrylate. Examples of suitable hydroxyalkyl esters with secondary hydroxyl groups are 2-hydroxypropyl(meth)acrylate, 2-hydroxybutyl(meth)acrylate, 3-hydroxybutyl(meth)acrylate.

Preferred are hydroxy functional acrylic polymers having a hydroxy equivalent weight of 300 to 1300 and are polymers of hydroxy alkyl (meth)acrylates and one or more of the aforementioned monomers. The hydroxyl equivalent weight is the grams of resin per equivalent of hydroxyl groups. The following are typically preferred acrylic polymers: styrene/methyl methacrylate/isobutyl methacrylate/hydroxyethyl (meth) acrylate; styrene/methyl methacrylate/isobutyl methacrylate/ 2-ethylhexyl methacrylate/isobornyl methacrylate/hydroxyethyl (meth)acrylate and styrene/isobornyl methacrylate/2-ethylhexyl methacrylate/hydroxy propyl methacrylate/ hydroxyethyl(meth)acrylate. One particularly preferred hydroxy containing acrylic polymer contains 35 to 50 percent by weight styrene, 15 to 25 percent by weight ethylhexyl methacrylate and 15 to 20 percent by weight isobornyl methacrylate and 20 to 30 percent by weight hydroxyethyl methacrylate.

Additional useful hydroxy-functional unsaturated monomers are reaction products of alpha,beta-unsaturated monocarboxylic acids with glycidyl esters of saturated monocarboxylic acids branched in alpha position, for example with glycidyl esters of saturated alpha-alkylalkanemonocarboxylic acids or alpha,alpha'-dialkylalkanemonocarboxylic acids. These preferably comprise the reaction products of (meth) acrylic acid with glycidyl esters of saturated alpha,alpha-dialkylalkanemonocarboxylic acids with 7 to 13 carbon atoms per molecule, particularly preferably with 9 to 11 carbon atoms per molecule. These reaction products may be formed before, during or after the copolymerization reaction.

Further usable hydroxy-functional unsaturated monomers are reaction products of hydroxyalkyl(meth)acrylates with lactones. Hydroxyalkyl(meth)acrylates which may be used are, for example, those stated above. Suitable lactones are, for example, those that have 3 to 15 carbon atoms in the ring, wherein the rings may also comprise different substituents. Preferred lactones are gamma-butyrolactone, delta-valerolactone, epsilon-caprolactone, beta-hydroxy-beta-methyl-delta-valerolactone, lambda-laurolactone or mixtures thereof. Epsilon-caprolactone is particularly preferred. The reaction products preferably comprise those prepared from 1 mole of a hydroxyalkyl ester of an alpha,beta-unsaturated monocarboxylic acid and 1 to 5 moles, preferably on average 2 moles, of a lactone. The hydroxyl groups of the hydroxyalkyl esters may be modified with the lactone before, during or after the copolymerization reaction.

Suitable unsaturated monomers that can be used to provide the acrylic polymer with carboxyl groups are, for example, olefinically unsaturated monocarboxylic acids, such as, for example, acrylic acid, methacrylic acid, crotonic acid, isocrotonic acid, itaconic acid. Acrylic acid and methacrylic acid are preferably used.

Suitable unsaturated monomers that can be used to provide the acrylic polymer with glycidyl groups are, for example, allyl glycidyl ether, 3,4-epoxy-1-vinylcyclohexane, epoxycyclohexyl(meth)acrylate, vinyl glycidyl ether and glycidyl (meth)acrylate. Glycidyl(meth)acrylate is preferably used.

Free-radically polymerizable, olefinically unsaturated monomers which, apart from at least one olefinic double bond, do not contain additional functional groups that can be used to form the acrylic polymer are, for example, esters of unsaturated carboxylic acids with aliphatic monohydric branched or unbranched as well as cyclic alcohols with 1 to 20 carbon atoms. The unsaturated carboxylic acids, which may be considered, are acrylic acid, methacrylic acid, crotonic acid and isocrotonic acid. Esters of (meth)acrylic acid are preferred.

The acrylic polymer can contain (meth)acrylamides. Typical examples of such acrylic polymers are polymers of (meth) acrylamide and alkyl(meth)acrylates, hydroxy alkyl(meth) acrylates, (meth)acrylic acid and or one of the aforementioned ethylenically unsaturated polymerizable monomers.

Acrylic oligomers having a number average molecular weight of 300 to 3,000 of the aforementioned monomeric components also can be used as an optional polymeric component. Useful acrylic oligomers are disclosed in U.S. Ser. No. 10/617,585 filed Jul. 11, 2003. By using monomers and reactants well known to those skilled in the art, these oligomers can have the one or more of the following groups that are reactive with isocyanate: hydroxyl, carboxyl, glycidyl, amine, aldimine, phosphoric acid and ketimine.

Acrylourethanes also can be used to form the novel coating composition of this invention. Typical useful acrylourethanes are formed by reacting the aforementioned acrylic polymers with an organic polyisocyanate. Generally, an excess of the acrylic polymer is used so that the resulting acrylourethane has terminal acrylic segments having reactive groups as described above. These acrylourethanes can have reactive end groups and/or pendant groups such as hydroxyl, carboxyl, amine, glycidyl, amide, silane or mixtures of such groups. Useful organic polyisocyanates are described hereinafter as the crosslinking component but also can be used to form acrylourethanes useful in this invention. Typically useful acrylourethanes are disclosed in Stamegna et al. U.S. Pat. No. 4,659,780, which is hereby incorporated by reference.

Polyesters can also be used, such as, hydroxyl or carboxyl terminated or hydroxyl or carboxyl containing polyesters. The following are typically useful polyesters or ester oligomers: polyesters or oligomers of caprolactone diol and cyclohexane dimethylol, polyesters or oligomers of tris-hydroxy ethylisocyanurate and caprolactone, polyesters or oligomers of trimethylol propane, phthalic acid or anhydride and ethylene oxide, polyesters or oligomers of pentaerythritol, hexahydrophthalic anhydride and ethylene oxide, polyesters or oligomers of pentaerythritol, hexahydrophthalic anhydride and butylene oxide as disclosed in U.S. Pat. No. 6,221,484 B1.

The aforementioned polyesters and oligomers can be reacted with an organic isocyanate to form polyesterurethane polymers and oligomers that can be used in the novel composition.

One useful polyesterurethane that can used in the composition is formed by reacting an aliphatic polyisocyanate with an aliphatic or cycloaliphatic monohydric alcohol and subsequently reacting the resulting composition with a hydroxy functional aliphatic carboxylic acid until all of the isocyanate groups have been reacted. One useful polyurethane oligomer comprises the reaction product of the isocyanurate of hexane diisocyanate, cyclohexanol and dimethylol propionic acid.

Useful branched copolyesters polyols and the preparation thereof are described in WO 03/070843 published Aug. 28, 2003, which is hereby incorporated by reference.

The branched copolyester polyol has a number average molecular weight not exceeding 30,000, alternately in the range of from 1,000 to 30,000, further alternately in the range of 2,000 to 20,000, and still further alternately in the range of 5,000 to 15,000. The copolyester polyol has hydroxyl groups ranging from 5 to 200 per polymer chain, preferably 6 to 70, and more preferably 10 to 50, and carboxyl groups ranging from 0 to 40 per chain, preferably 1 to 40, more preferably 1 to 20 and most preferably 1 to 10. The Tg (glass transition temperature) of the copolyester polyol ranges from −70° C. to 50° C., preferably from −65° C. to 40° C., and more preferably from −60° C. to 30° C.

The branched copolyester polyol is conventionally polymerized from a monomer mixture containing a chain extender selected from the group consisting of a hydroxy carboxylic acid, a lactone of a hydroxy carboxylic acid and a combination thereof; and one or more hyper branching monomers.

The following additional ingredients can be included in the coating composition, particularly when the coating composition is useful as a lacquer, in amounts of 0.1% to 98% by weight and alternately in the range of 50% to 95% by weight, all based on the weight of the binder of the coating composition.

Useful acrylic alkyd polymers having a weight average molecular weight ranging from 3,000 to 100,000 and a Tg ranging from 0° C. to 100° C. are conventionally polymerized from a monomer mixture that can include one or more of the following monomers: an alkyl(meth)acrylate, for example, methyl(meth)acrylate, butyl(meth)acrylate, ethyl(meth)acrylate, 2-ethyl hexyl(meth)acrylate; a hydroxy alkyl(meth) acrylate, for example, hydroxy ethyl(meth)acrylate, hydroxy propyl(meth)acrylate, hydroxy butyl (meth)acrylate; (meth) acrylic acid; styrene; and alkyl amino alkyl (meth)acrylate, for example, diethylamino ethyl(meth)acrylate or t-butyl aminoethyl methacrylate; and one or more of the following drying oils: vinyl oxazoline drying oil esters of linseed oil fatty acids, tall oil fatty acids or tung oil fatty acids.

One preferred polymer is polymerized from a monomer mixture that contains an alkyl(meth)acrylate, hydroxy alkyl acrylate, alkylamino alkyl acrylate and vinyl oxazoline ester of drying oil fatty acids.

Suitable iminiated acrylic polymers can be obtained by reacting acrylic polymers having carboxyl groups with an alkylene imine, such as propylene imine.

Suitable cellulose acetate butyrates are supplied by Eastman Chemical Co., Kingsport, Tenn. under the trade names CAB-381-20 and CAB-531-1 and are preferably used in an amount of 0.1 to 20 percent by weight based on the weight of the binder.

A suitable ethylene-vinyl acetate co-polymer (wax) is supplied by Honeywell Specialty Chemicals—Wax and Additives, Morristown, N.J., under the trade name A-C® 405 (T) Ethylene—Vinyl Acetate Copolymer.

Suitable nitrocellulose resins preferably have a viscosity of about ½-6 seconds. Preferably, a blend of nitrocellulose resins is used. Optionally, the lacquer can contain ester gum and castor oil.

Suitable alkyd resins are the esterification products of a drying oil fatty acid, such as linseed oil and tall oil fatty acid, dehydrated castor oil, a polyhydric alcohol, a dicarboxylic acid and an aromatic monocarboxylic acid. Typical polyhydric alcohols that can be used to prepare the alkyd resin used in this invention are glycerine, pentaerythritol, trimethylol ethane, trimethylol propane; glycols, such as ethylene glycol, propylene glycol, butane diol and pentane diol. Typical dicarboxylic acids or anhydrides that can be used to prepare the alkyd resin are phthalic acid, phthalic anhydride, isophthalic acid, terephthalic acid maleic, and fumaric acid. Typical monocarboxylic aromatic acids are benzoic acid, paratertiary butylbenzoic acid, phenol acetic acid and triethyl benzoic acid. One preferred alkyd resin is a reaction product of an acrylic polymer and an alkyd resin.

Useful carbamate containing polymers are disclosed in U.S. Patent Application Publication 2003/0050388, which is hereby incorporated by reference and in particular discloses a carbamate polymer comprises the reaction product of an aliphatic polyisocyanate, a monohydric alcohol, a hydroxyfunctional aliphatic carboxylic acid and a polyalkylene ether glycol and has a number average molecular weight in the range of 100 to 2000. Other useful carbamate functional polymers are disclosed in Ramesh et al. U.S. Pat. No. 6,462,144 B1, which is hereby incorporated by reference and shows a carbamate functional polymer having a hyperbranched or star polyol core, a first chain extension based on a polycarboxylic acid or anhydride, a second chain extension based on an epoxy containing compound, and having carbamate functional groups on the core, the second chain extension or both. Acrylic polymers having primary functional carbamate functionality are useful and are disclosed in U.S. Pat. No. 5,866,259, which is hereby incorporated by reference.

Suitable plasticizers include butyl benzyl phthalate, dibutyl phthalate, triphenyl phosphate, 2-ethylhexylbenzyl phthalate, dicyclohexyl phthalate, diallyl toluene phthalate, dibenzyl phthalate, butylcyclohexyl phthalate, mixed benzoic acid and fatty oil acid esters of pentaerythritol, poly(propylene adipate) dibenzoate, diethylene glycol dibenzoate, tetrabutylthiodisuccinate, butyl phthalyl butyl glycolate, acetyltributyl citrate, dibenzyl sebacate, tricresyl phosphate, toluene ethyl sulfonamide, the di-2-ethyl hexyl ester of hexamethylene diphthalate, and dimethyl cyclohexyl)phthalate. One preferred plasticizer of this group is butyl benzyl phthalate.

If desired, the coating composition can include metallic driers, chelating agents, or a combination thereof. Suitable organometallic driers include cobalt naphthenate, copper naphthenate, lead tallate, calcium naphthenate, iron naphthenate, lithium naphthenate, lead naphthenate, nickel octoate, zirconium octoate, cobalt octoate, iron octoate, zinc octoate, and alkyl tin dilaurates, such as dibutyl tin dilaurate. Suitable chelating agents include aluminum monoisopropoxide monoversatate, aluminum (monoiospropyl)phthalate, aluminum diethoxyethoxide monoversatate, aluminum trisecondary butoxide, aluminum diisopropoxide monoacetacetic ester chelate and aluminum isopropoxide.

Also, polytrimethylene ether diols may be used as an additive having a number average molecular weight (Mn) in the range of from 500 to 5,000, alternately in the range of from 1,000 to 3,000; a polydispersity in the range of from 1.1 to 2.1 and a hydroxyl number in the range of from 20 to 200. The preferred polytrimethylene ether diol has a Tg of −75° C. Copolymers of polytrimethylene ether diols are also suitable. For example, such copolymers are prepared by copolymerizing 1,3-propanediol with another diol, such as, ethane diol, hexane diol, 2-methyl-1,3-propanediol, 2,2-dimethyl-1,3-propanediol, trimethylol propane and pentaerythritol, wherein at least 50 percent of the copolymer results from 1,3-propanediol. A blend of a high and low molecular weight polytrimethylene ether diol can be used wherein the high molecular weight diol has an Mn ranging from 1,000 to 4,000 and the low molecular weight diol has an Mn ranging from 150 to 500. The average Mn of the diol should be in the range of 1,000 to 4,000. It should be noted that, the polytrimethylene ether diols suitable for use in the present invention can include polytrimethylene ether triols and other higher functionality polytrimethylene ether polyols in an amount ranging from 1 to 20%, by weight, based on the weight of the polytrimethylene ether diol. It is believed that the presence of polytrimethylene ether diols in the crosslinked coating composition of this invention can improve the chip resistance of a coating resulting therefrom.

Additional details of the foregoing additives are provided in U.S. Pat. No. 3,585,160, U.S. Pat. No. 4,242,243, U.S. Pat. No. 4,692,481, and U.S. Re 31.309, which are incorporated therein by reference.

Crosslinking Agents

Lacquer coating compositions can be formulated without the use of a crosslinking agent. Typical crosslinkable compositions that utilize the novel rheology control agents are solvent borne or water borne compositions having a binder containing in the range of 25-95 percent by weight of the aforementioned film forming polymer and 5-75 percent by weight of a crosslinking agent. Preferably, the binder contains in the range of 40-90 percent by weight of the film forming polymer and 10-60 percent by weight of the crosslinking agent. Useful crosslinking agents include organic polyisocyanates, blocked organic polyisocyanates, melamines, alkylated melamines, benzoquanamines, epoxides and silanes Typically useful organic polyisocyanates crosslinking agents that can be used in the novel composition of this invention include aliphatic polyisocyanates, cycloaliphatic polyisocyanates and isocyanate adducts. Typical polyisocyanates can contain within the range of 2 to 10, preferably 2.5 to 8, more preferably 3 to 5 isocyanate functionalities. Generally, the ratio of equivalents of isocyanate functionalities on the polyisocyanate per equivalent of all of the functional groups present ranges from 0.5/1 to 3.0/1, preferably from 0.7/1 to 1.8/1, more preferably from 0.8/1 to 1.3/1.

Examples of suitable aliphatic and cycloaliphatic polyisocyanates that can be used include the following: 4,4'dicyclohexyl methane diisocyanate, ("$H_{12}$MDI"), trans-cyclohexane-1,4-diisocyanate, 1,6-hexamethylene diisocyanate ("HDI"), isophorone diisocyanate, ("IPDI"), other aliphatic or cycloaliphatic di-, tri- or tetra-isocyanates, such as, 1,2-propylene diisocyanate, tetramethylene diisocyanate, 2,3-butylene diisocyanate, octamethylene diisocyanate, 2,2,4-trimethyl hexamethylene diisocyanate, dodecamethylene diisocyanate, omega-dipropyl ether diisocyanate, 1,3-cyclopentane diisocyanate, 1,2 cyclohexane diisocyanate, 1,4 cyclohexane diisocyanate, 4-methyl-1,3-diisocyanatocyclohexane, dicyclohexylmethane-4,4'-diisocyanate, 3,3'-dimethyl-dicyclohexylmethane 4,4'-diisocyanate, polyisocyanates having isocyanurate structural units, such as, the isocyanurate of hexamethylene diisocyanate and the isocyanurate of isophorone diisocyanate, the adduct of 2 molecules of a diisocyanate, such as, hexamethylene diisocyanate, uretidiones of hexamethylene diisocyanate, uretidiones of isophorone diisocyanate and a diol, such as, ethylene glycol, the adduct of 3 molecules of hexamethylene diisocyanate and 1 molecule of water, allophanates, trimers and biurets of hexamethylene diisocyanate, allophanates, trimers and biurets of isophorone diisocyanate and the isocyanurate of hexane diisocyanate.

Tri-functional isocyanates also can be used, such as, Desmodur® N 3300, trimer of hexamethylene diisocyanate, Desmodur® 3400, trimer of isophorone diisocyanate, Desmodur® 4470 trimer of isophorone diisocyanate, these trimers are sold by Bayer Corporation. A trimer of hexamethylene diisocyanate sold as Tolonate® HDT from Rhodia Corporation is also suitable.

An isocyanate functional adduct can be used, such as, an adduct of an aliphatic polyisocyanate and a polyol. Also, any of the aforementioned polyisocyanates can be used with a polyol to form an adduct. Polyols, such as, trimethylol alkanes, particularly, trimethylol propane or ethane can be used to form an adduct.

The melamine crosslinking agents are generally partially alkylated melamine formaldehyde compounds and may be monomeric or polymeric or mixtures thereof. Some of the suitable monomeric melamines include low molecular weight melamines which contain, on an average, three or more methylol groups etherized with a $C_1$ to $C_5$ monohydric alcohol such as methanol, n-butanol, or isobutanol per triazine nucleus, and have an average degree of condensation up to about 2 and preferably in the range of about 1.1 to about 1.8, and have a proportion of mononuclear species not less than about 50 percent by weight. By contrast the polymeric melamines have an average degree of condensation of more than 1.9.

Some such suitable monomeric melamines include alkylated melamines, such as methylated, butylated, isobutylated melamines and mixtures thereof. Many of these suitable monomeric melamines are supplied commercially. For example, Cytec Industries Inc., West Patterson, N.J. supplies Cymel® 301 (degree of polymerization of 1.5, 95% methyl and 5% methylol), Cymel® 350 (degree of polymerization of 1.6, 84 percent methyl and 16 percent methylol), 303, 325, 327 and 370, which are all monomeric melamines. Suitable polymeric melamines include high amino (partially alkylated) melamine known as Resimene® BMP5503 (molecular weight 690, polydispersity of 1.98, 56 percent butyl, 44 percent amino), which is supplied by Solutia Inc., St. Louis, Mo., or Cymel®1158 provided by Cytec Industries Inc., West Patterson, N.J. Cytec Industries Inc. also supplies Cymel® 1130@80 percent solids (degree of polymerization of 2.5), Cymel® 1133 (48 percent methyl, 4 percent methylol and 48 percent butyl), both of which are polymeric melamines.

If desired, appropriate catalysts may also be included in the activated compositions to accelerate the curing process of a potmix of the coating composition.

When the activated compositions include melamine as the crosslinking agent, it also preferably includes a catalytically active amount of one or more acid catalysts to further enhance the crosslinking of the components on curing. Generally, catalytically active amount of the acid catalyst in the coating composition ranges from about 0.1 percent to about 5 percent, preferably ranges from 0.1 percent to 2 percent, more preferably ranges from 0.5 percent to 1.2 percent, all in weight percent based on the weight of the binder. Some suitable acid catalysts include aromatic sulfonic acids, such as dodecylbenzene sulfonic acid, para-toluenesulfonic acid and dinonylnaphthalene sulfonic acid, all of which are either unblocked or blocked with an amine, such as dimethyl oxazolidine and 2-amino-2-methyl-1-propanol, n,n-dimethylethanolamine or a combination thereof. Other acid catalysts that can be used, such as phosphoric acids, more particularly, phenyl acid phosphate, benzoic acid, oligomers having pendant acid groups, all of which may be unblocked or blocked with an amine.

When the activated compositions include a polyisocyanate as the crosslinking agent, the coating composition preferably includes a catalytically active amount of one or more tin or tertiary amine catalysts for accelerating the curing process. Generally, catalytically active amount of the catalyst in the coating composition ranges from about 0.001 percent to about 5 percent, preferably ranges from 0.005 percent to 2 percent, more preferably ranges from 0.01 percent to 1 percent, all in weight percent based on the weight of the binder. A wide variety of catalysts can be used, such as, tin compounds, including dibutyl tin dilaurate and dibutyl tin diacetate; tertiary amines, such as, triethylenediamine. These catalysts can be used alone or in conjunction with carboxylic acids, such as, acetic acid. One of the commercially available catalysts, sold under the trademark, Fastcat® 4202 dibutyl tin dilaurate by Elf-Atochem North America, Inc. Philadelphia, Pa., is particularly suitable.

Carrier Medium

The liquid carrier medium comprises an organic solvent or blend of solvents or an aqueous carrier comprising water and optionally, compatible organic solvents. The coating compositions contain about 5-95 percent, more typically 10-85 percent by weight of solvent, and about 5-95 percent, more typically 15-90 percent by weight, of an organic liquid carrier (based on the weight of the coating composition). The selection of organic solvent depends upon the requirements of the specific end use application of the coating composition of this invention, such as the VOC emission requirements, the selected pigments, binder and crosslinking agents. Representative examples of organic solvents which are useful herein include alcohols, such as methanol, ethanol, n-propanol, and isopropanol; ketones, such as acetone, butanone, pentanone, hexanone, and methyl ethyl ketone, methyl isobutyl ketone, diisobutyl ketone, methyl amyl ketone; alkyl esters of acetic, propionic, and butyric acids, such as ethyl acetate, butyl acetate, and amyl acetate; ethers, such as tetrahydrofuran, diethyl ether, and ethylene glycol and polyethylene glycol monoalkyl and dialkyl ethers, such as cellosolves and carbitols; and glycols, such as ethylene glycol and propylene glycol and mixtures thereof, and aromatic hydrocarbon solvents, such as xylene, toluene. Typically, aqueous carriers comprise water and a blend of organic solvents suited for the requirements of the coating composition.

Pigments

The novel coating composition may be used as a base coat or as a pigmented mono-coat topcoat. Both of these compositions require the presence of pigments. Typically, a pigment-to-binder ratio of 0.1/100 to 200/100 is used depending on the color and type of pigment used. The pigments are formulated into mill bases by conventional procedures, such as, grinding, sand milling, ball milling, high speed mixing, attritor grinding and two or three roll milling. Generally, the mill base comprises pigment and a dispersant in a liquid carrier. The mill base is added in an appropriate amount to the coating composition with mixing to form a pigmented coating composition.

Any of the conventionally-used organic and inorganic pigments, such as, white pigments, like, titanium dioxide, color pigments, metallic flakes, such as, aluminum flake, special effects pigments, such as, coated mica flakes, coated aluminum flakes and the like, azo, anthraquinone, thioindigo, oxazine, quinacridone, lakes and toners of acidic dye stuffs, copper phthalocyanine and its derivatives, and various mixtures and modifications thereof and extender pigments can be used.

The novel coating composition may be used as a primer, primer surfacer, or sealer in which case typical pigments used in primers would be added, such as, carbon black, barytes, silica, iron oxide and other pigments that are commonly used in primers in a pigment-to-binder ratio of 10/100 to 300/100.

Coating Compositions and Additives to Improve Weatherability

Coating composition formulated with the novel rheology control agent of this invention can be used as a clear coat that is applied over a pigmented base coat that may be a pigmented version of the composition of this invention or another type of a pigmented base coat. The clear coating can be in solution or in dispersion form.

Typically, a clear coating is applied over the base coating before the base coating is fully cured. This is a so called "wet-on-wet process". In this process, a base coating is applied to a substrate and flash dried and then the clear coating is applied and both layers are then fully cured either at ambient temperatures or cured by heating to elevated temperatures, for example, of 50° C. to 150° C. for 15 to 45 minutes to form a clear coat/base coat finish. When used in combination with a primer or primer-surfacer, the primer or primer-surfacer is also flash dried and then the base coating and clear coating are applied as above. This is a so-called "wet on wet on wet" process. The base coating and clear coating preferably have a dry coating thickness ranging from 25 to 75 microns and 25 to 100 microns, respectively.

When refinishing automobile and truck bodies, the original OEM topcoat is usually sanded and a primer or sealer coat applied and then a mono coat or a basecoat/clear coat is applied. These coatings are usually cured at ambient temperatures or at slightly elevated temperatures, such as, 40 to 100° C.

To improve the weathering properties of clear coatings, the novel coating composition contains about 0.1 to 5 percent by weight, based on the weight of the binder, of ultraviolet light absorbers. Typically useful ultraviolet light absorbers include hydroxyphenyl benzotriazols, such as, 2-(2-hydroxy-5-methylphenyl)-2H-benzotrazole, 2-(2-hydroxy-3,5-di-tert.amylphenyl)-2H-benzotriazole, 2[2-hydroxy-3,5-di(1,1-dimethylbenzyl)phenyl]-2H-benzotriazole, reaction product of 2-(2-hydroxy-3-tert.butyl-5-methyl propionate)-2H-benzotriazole and polyethylene ether glycol having a weight average molecular weight of 300, 2-(2-hydroxy-3-tert.butyl-5-iso-octyl propionate)-2H-benzotriazole; hydroxyphenyl s-triazines, such as, 2-[4((2,-hydroxy-3-dodecyloxy/tridecyloxypropyl)-oxy)-2-hydroxyphenyl]-4,6-bis(2,4-dimethylphenyl)-1,3,5-triazine, 2-[4(2-hydroxy-3-(2-ethylhexyl)-oxy)-2-hydroxyphenyl]-4,6-bis(2,4-dimethylphenyl)1,3,5-triazine, 2-(4-octyloxy-2-hydroxyphenyl)-4,6-bis(2,4-dimethylphenyl)-1,3,5-triazine; hydroxybenzophenone U.V. absorbers, such as, 2,4-dihydroxybenzophenone, 2-hydroxy-4-octyloxybenzophenone, and 2-hydroxy-4-dodecyloxybenzophenone.

These clear coating compositions also may contain about 0.1 to 5 percent by weight, based on the weight of the binder, of a di-substituted phenol antioxidant or a hydroperoxide decomposer. Typically useful antioxidants include tetrakis[methylene(3,5-di-tert-butylhydroxy hydrocinnamate)] methane, octadecyl 3,5-di-tert-butyl-4-hydroxyhydrocinnamate, tris(2,4-di-tert-butylphenyl) phosphite, 1,3,5-tris(3,5-di-tert-butyl-4-hydroxybenzyl)-1,3,5-triazine-2,4,6(1H,3H,5H)-trione and benzenepropanoic acid, 3,5-bis(1,1-dimethyl-ethyl)-4-hydroxy-C7-C9 branched alkyl esters. Typically useful hydroperoxide decomposers include Sanko® HCA (9,10-dihydro-9-oxa-10-phosphenanthrene-10-oxide), triphenyl phosphate and other organo-phosphorous compounds, such as, Irgafos® TNPP from Ciba Specialty Chemicals, Irgafos® 168, from Ciba Specialty Chemicals, Ultranox® 626 from GE Specialty Chemicals, Mark PEP-6 from Asahi Denka, Mark HP-10 from Asahi Denka, Irgafos® P-EPQ from Ciba Specialty Chemicals, Ethanox 398 from Albemarle, Weston 618 from GE Specialty Chemicals, Irgafos® 12 from Ciba Specialty Chemicals, Irgafos® 38 from Ciba Specialty Chemicals, Ultranox® 641 from GE Specialty Chemicals and Doverphos® S-9228 from Dover Chemicals.

These clear coating compositions also may contain about 0.1-5 percent by weight, based on the weight of the binder, of hindered amine light stabilizers. Typically useful hindered amine light stabilizers include N-(1,2,2,6,6-pentamethyl-4-piperidinyl)-2-dodecyl succinimide, N(1acetyl-2,2,6,6-tetramethyl-4-piperidinyl)-2-dodecyl succinimide, N-(2hydroxyethyl)-2,6,6,6-tetramethylpiperidine-4-ol-succinic acid copolymer, 1,3,5 triazine-2,4,6-triamine, N,N'''-[1,2-ethanediybis[[[4,6-bis[butyl(1,2,2,6,6-pentamethyl-4-piperidinyl)amino]-1,3,5-triazine-2-yl]imino]-3,1-propanediyl]]bis[N,N'''-dibutyl-N',N'''-bis(1,2,2,6,6-pentamethyl-4-piperidinyl)], poly-[[6-[1,1,3,3-tetramethylbutyl)-amino]-1,3,5-trianzine-2,4-diyl][2,2,6,6-tetramethylpiperidinyl)-imino]-1,6-hexane-diyl[(2,2,6,6-tetramethyl-4-piperidinyl)-imino]), bis(2,2,6,6-tetramethyl-4-piperidinyl)sebacate, bis(1,2,2,6,6-pentamethyl-4-piperidinyl)sebacate, bis(1-octyloxy-2,2,6,6-tetramethyl-4-piperidinyl)sebacate, bis(1,2,2,6,6-pentamethyl-4-piperidinyl)[3,5bis(1,1-dimethylethyl-4-hydroxy-phenyl)methyl]butyl propanedioate, 8-acetyl-3-dodecyl-7,7,9,9,-tetramethyl-1,3,8-triazaspiro(4,5)decane-2,4-dion, dodecyl/tetradecyl-3-(2,2,4,4-tetramethyl-2l-oxo-7-oxa-3,20-diazaldispiro(5.1.11.2)henicosan-20-yl)propionate.

Other Additives

In addition, coating composition utilizing the rheology control agent of this invention may contain a variety of other optional ingredients, including fillers, plasticizers, antioxidants, surfactants and flow control agents.

For example, the novel composition can contain 0.1 to 30 percent by weight, based on the weight of the binder, of acrylic NAD (non-aqueous dispersed) resins. These NAD resins typically are high molecular weight resins having a crosslinked acrylic core with a Tg between 20 to 100° C. and attached to the core are low Tg stabilizer segments. A description of such NADs is found in Antonelli et al. U.S. Pat. No. 4,591,533 and in Barsotti et al. U.S. Pat. No. 5,763,528 which patents are hereby incorporated by reference.

Also, these coating composition may include other conventional formulation additives known to those skilled in the art, such as, wetting agents, leveling and flow control agents, for example, Resiflow®S (polybutylacrylate), BYK® 320 and 325 (high molecular weight polyacrylates), BYK® 347 (polyether-modified siloxane), rheology control agents, such as, fumed silica, defoamers, surfactants and emulsifiers to help stabilize the composition. Other additives that tend to improve mar resistance can be added, such as, silsesquioxanes and other silicate-based micro-particles.

One particularly useful additive is a blend of the novel rheology control agent and finely divided silica in a weight ratio of 0.1:1 to 1:0.1. Other particularly useful additive is a blend of the novel rheology control agent and bis-urea crystals as mentioned in U.S. Pat. No. 4,311,622 in a weight ratio of 0.1:1 to 1:0.1.

The rheology control agent may be incorporated into one of the components of a typical two component (2K) coating composition. For example, in a typical 2K acrylic/isocyanate system, the rheology control agent may be incorporated with the acrylic polymer component which is then blended with the isocyanate component just before application.

Application

Coating composition containing the novel rheology control agent can be applied by conventional techniques, such as, spraying, electrostatic spraying, dipping, brushing, and flow coating. Spraying and electrostatic spraying are preferred methods of application.

In OEM applications, the composition is typically baked at 60°-150° C. for about 15-30 minutes to form a coating about 2.5-75 microns thick. When the composition is used in a base coat/clear coat system, the basecoat may be dried to a tack-free state and cured or preferably flash dried for a short period before the clear coat is applied (wet-on-wet). The base coat/clear coat finish is then baked as mentioned above to provide a dried and cured finish. The novel coating composition can also be formulated with the 3-wet (wet-on-wet-on-wet) coating process, where the primer, basecoat and clearcoat are applied in sequential steps without baking process in between each layer. The final coating is then baked to provide a dried and cure finish. The present invention is also applicable to non-baking refinish systems, as will be readily appreciated by those skilled in the art.

If used in refinishing vehicles, the base coat may be allowed to "dry to the touch" at ambient temperature conditions or under warm air before the clear coating is applied. The base coating and clear coating preferably have a dry coating thickness ranging from 25 to 75 microns and 25 to 100 microns, respectively. These coatings are usually cured at ambient temperatures or at slightly elevated temperatures, such as, 40 to 100° C.

These coating compositions are particularly useful for the repair and refinish of automobile bodies and truck bodies and parts as a clear coat, pigmented base coat, as a primer surfacer or primer filler. The novel composition has uses for coating any and all items manufactured and painted by automobile sub-suppliers, frame rails, commercial trucks and truck bodies, including but not limited to beverage bottles, utility bodies, ready mix concrete delivery vehicle bodies, waste hauling vehicle bodies, and fire and emergency vehicle bodies, as well as any potential attachments or components to such truck bodies, buses, farm and construction equipment, truck caps and covers, commercial trailers, consumer trailers, recreational vehicles, including but not limited to, motor homes, campers, conversion vans, vans, large commercial aircraft and small pleasure aircraft, pleasure vehicles, such as, snow mobiles, all terrain vehicles, personal watercraft, motorcycles, and boats. The novel composition also can be used as a coating for industrial and commercial new construction and maintenance thereof; cement and wood floors; walls of commercial and residential structures, such as, office buildings and homes; amusement park equipment; concrete surfaces, such as parking lots and drive ways; asphalt and concrete road surface, wood substrates, marine surfaces; outdoor structures, such as bridges, towers; coil coating; railroad cars; printed circuit boards; machinery; OEM tools; signs; fiberglass structures; sporting goods; and sporting equipment.

The present invention is further defined in the following Examples. It should be understood that these Examples are given by way of illustration only. From the above discussion and these Examples, one skilled in the art can ascertain the essential characteristics of this invention, and without departing from the spirit and scope thereof, can make various changes and modifications of the invention to adapt it to various uses and conditions. As a result, the present invention is not limited by the illustrative examples set forth herein below, but rather is defined by the claims contained herein below.

The following Examples illustrate the invention. All parts and percentages are on a weight basis unless otherwise indicated. All molecular weights disclosed herein are determined by LC/MS (Liquid Chromatography/Mass Spectroscopy).

EXAMPLES

Example 1

The following reaction was carried out under a blanket of nitrogen. An organic diisocyanate of 23.18 g (0.1092 mol) of lysine diisocyanate methyl ester was added drop-wise into a flask equipped with a stirrer containing 37.05 g (0.2163 mol) undecyl amine in 700 mL of chloroform and the reaction mixture was held at room temperature for about 2 hours with constant stirring. The reaction mixture was monitored with an IR spectrophotometer and when the isocyanate peak (about 2258 cm$^{-1}$) disappeared the reaction was considered completed and the reaction mixture was filtered to remove the product formed and any residual solvent was removed under vacuum. The yield was 53.89 g, 89.8% yield. The resulting rheology control agent had the following formula:

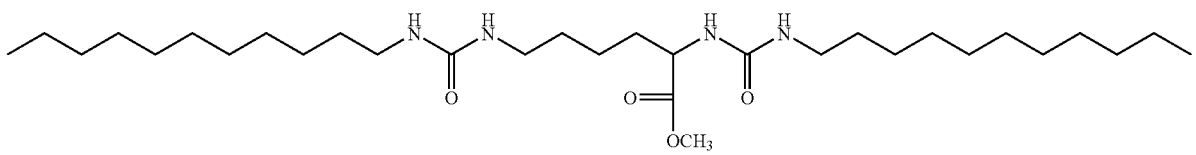

Example 2

The following reaction was carried out under a blanket of nitrogen. An organic diisocyanate of 14.53 g (0.068 mol) of lysine diisocyanate methyl ester was added drop-wise into a flask equipped with a stirrer containing 25 g (0.1334 mol) N-cyclohexyl-(2-hydroxyethyl)urea and 0.08 g of dibutyltindilaurate in 340 mL of acetonitrile and the reaction mixture was refluxed at 78° C. for about 2 hours with constant stirring. The reaction mixture was monitored with an IR spectrophotometer and when the isocyanate peak (about 2258 cm$^{-1}$) disappeared the reaction was considered completed and the reaction mixture was filtered to remove the product formed and any residual solvent was removed under vacuum. The yield was 36.79 g, 94.3% yield. The resulting rheology control agent had the following formula:

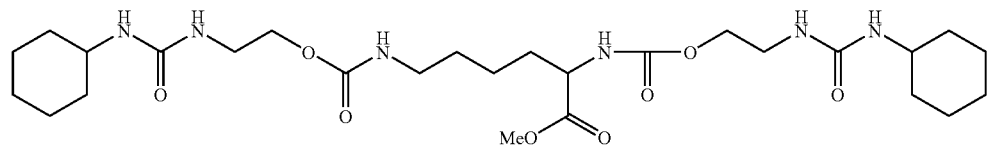

Example 3

The following reaction was carried out under a blanket of nitrogen. An organic diisocyanate of 2.01 g (0.0095 mol) of lysine diisocyanate methyl ester was added drop-wise into a flask equipped with a stirrer containing 4.03 g (0.0186 mol) N-hexyl-(2-hydroxyethyl)urea and 0.01 g of dibutyltindilaurate in 50 mL of acetonitrile and the reaction mixture was refluxed at 78° C. for about 2 hours with constant stirring. The reaction mixture was monitored with an IR spectrophotometer and when the isocyanate peak (about 2258 cm$^{-1}$) disappeared the reaction was considered completed and the reaction mixture was filtered to remove the product formed and any residual solvent was removed under vacuum. The yield was 5.24 g, 87.3% yield. The resulting rheology control agent had the following formula:

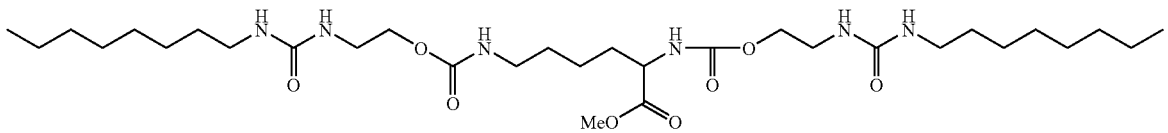

Example 4

The following reaction was carried out under a blanket of nitrogen. An organic diisocyanate of 2.15 g (0.0101 mol) of lysine diisocyanate methyl ester was added drop-wise into a flask equipped with a stirrer containing 3.61 g (0.0199 mol) methyl 6-aminocaproate and 2.21 g of triethylamine (0.0219 mol) in 50 mL of methylene chloride and the reaction mixture was held at room temperature for about 2 hours with constant stirring. The reaction mixture was monitored with an IR spectrophotometer and when the isocyanate peak (about 2258 cm$^{-1}$) disappeared the reaction was considered completed and the reaction mixture was filtered to remove the product formed and any residual solvent was removed under vacuum. The yield was 4.23 g, 84.6% yield. The resulting rheology control agent had the following formula:

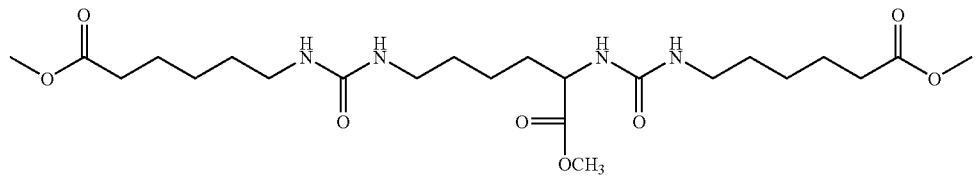

Example 5

The following reaction was carried out under a blanket of nitrogen. An organic diisocyanate of 2.27 g (0.0107 mol) of lysine diisocyanate methyl ester was added drop-wise into a flask equipped with a stirrer containing 3.52 g (0.0210 mol) ethyl 4-aminobutyrate hydrochloride and 2.34 g of triethylamine (0.0231 mol) in 50 mL of methylene chloride and the reaction mixture was held at room temperature for about 2 hours with constant stirring. The reaction mixture was monitored with an IR spectrophotometer and when the isocyanate peak (about 2258 cm$^{-1}$) disappeared the reaction was considered completed and the reaction mixture was filtered to remove the product formed and any residual solvent was removed under vacuum. The yield was 3.67 g, 73.7% yield. The resulting rheology control agent had the following formula:

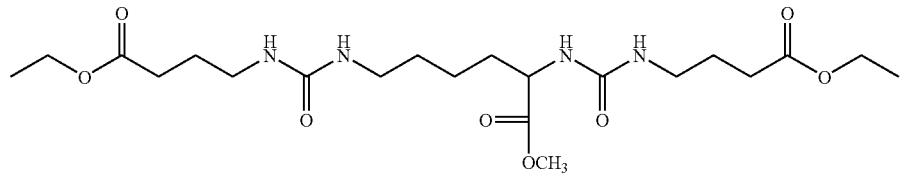

Example 6

The following reaction was carried out under a blanket of nitrogen. An organic diisocyanate of 2.05 g (0.0097 mol) of lysine diisocyanate methyl ester was added drop-wise into a flask equipped with a stirrer containing 1.22 g (0.0095 mol) octylamine in 30 mL of acetonitrile and the reaction mixture was held at room temperature for about 2 hours with constant stirring. 10 mL of N-methylpyrrolidinone (NMP) was added to the reaction mixture followed by the addition of a solution containing 10 mL NMP and 1.76 g N-cyclohexyl-(2-hydroxyethyl)urea (0.0095 mol). The reaction mixture was refluxed at 80° C. for 2 hours with constant stirring. The reaction mixture was monitored with an IR spectrophotometer and when the isocyanate peak (about 2258 cm$^{-1}$) disappeared the reaction was considered completed. The reaction mixture was precipitated out in water and filtered to remove the product formed and any residual solvent was removed under vacuum. The yield was 3.17 g, 63.4% yield. The resulting rheology control agent had the following formula:

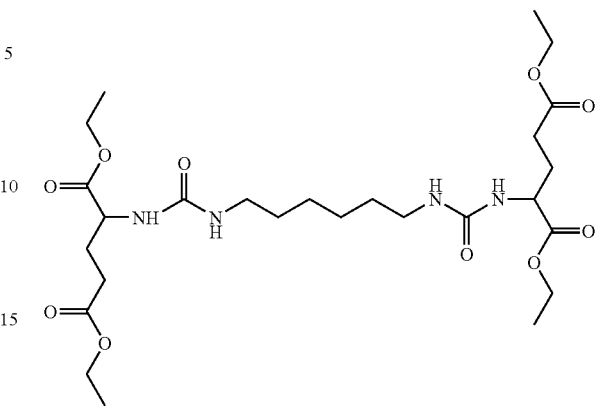

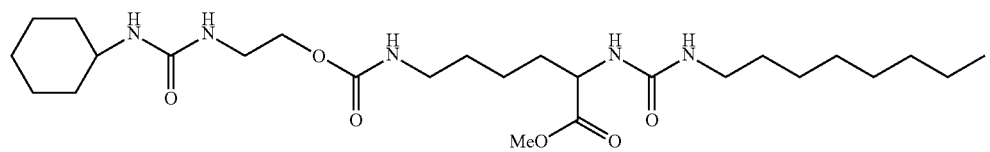

Example 7

The following reaction was carried out under a blanket of nitrogen. 1.60 g (9.995 mmol) of 1,6-diisocyanatohexane in 10 mL of chloroform was added drop-wise into a flask containing 3.88 g (19.1 mmol) diethyl 2-aminopentanedioate in 50 mL of chloroform. The flask was held at about 10° C. during the addition and was equipped with a stirrer. Then the reaction mixture was allowed to warm to room temperature and stirred for about 2 hours. The reaction mixture was monitored with an IR spectrophotometer and when the isocyanate peak (about 2258 cm$^{-1}$) disappeared the reaction was considered completed. The product was collected by filtration and subsequently drying under vacuum to give a white powder (5.4 g, 94.1% yield). The resulting rheology control agent had the following formula:

Example 8

The following reaction was carried out under a blanket of nitrogen. 12.61 g (75.0 mmol) of 1,6-diisocyanatohexane in 20 mL of toluene was added dropwise into a flask containing 40.10 g 2-(2-methoxyethoxy)ethyl 2-amino-3-phenylpropanoate in 80 mL of toluene. The flask was held at about 10° C. during the addition. The flask was equipped with a stirrer. The reaction mixture was allowed to warm to room temperature and stirred for overnight. The reaction mixture was monitored with an IR spectrophotometer and when the isocyanate peak (about 2258 cm$^{-1}$) disappeared the reaction was considered completed. The product was collected by filtration and subsequently drying under vacuum to give a white powder (45.1 g, 85.6% yield). The resulting rheology control agent had the following formula:

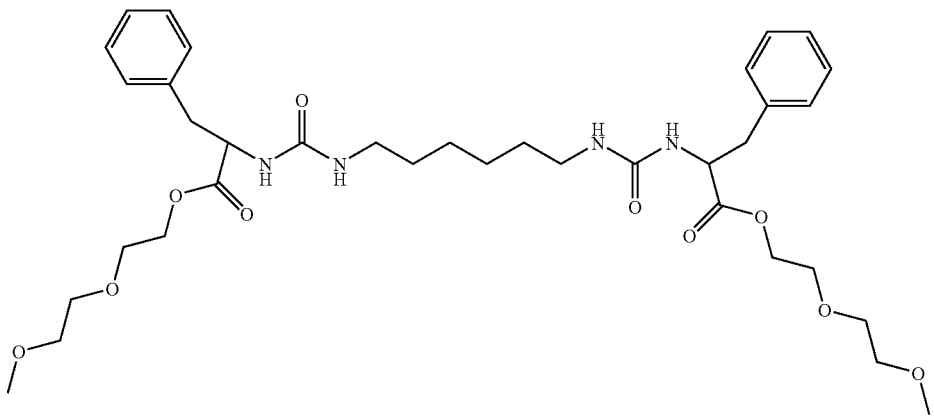

Example 9

The following reaction was carried out under a blanket of nitrogen. 1.26 g (7.50 mmol) of 1,6-diisocyanatohexane in 20 mL of toluene was added drop-wise into a flask containing 3.5 g 2-(2-methoxyethoxy)ethyl 2-amino-3-phenylpropanoate in 80 mL of toluene. The flask was held at about 10° C. during the addition. The flask was equipped with a stirrer. The reaction mixture was allowed to warm to room temperature and stirred for overnight. The reaction mixture was monitored with an IR spectrophotometer and when the isocyanate peak (about 2258 cm$^{-1}$) disappeared the reaction was considered completed. The product was collected by filtration and subsequently drying under vacuum to give a white powder (5.1 g, 96.8% yield). The resulting rheology control agent had the following formula:

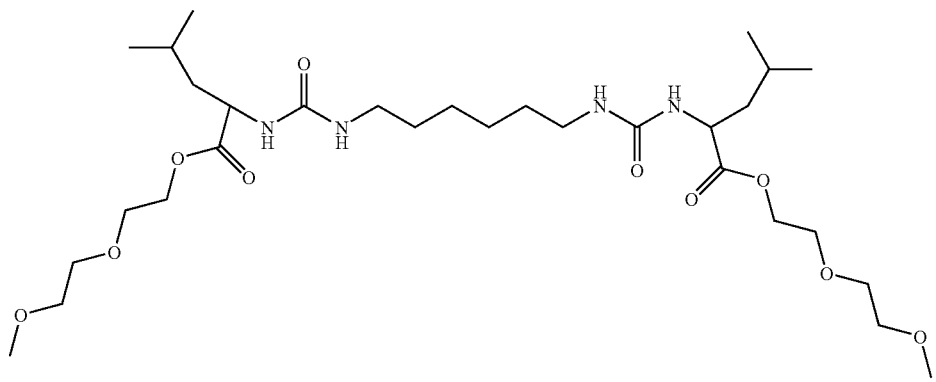

Example 10

The following reaction was carried out under a blanket of nitrogen. 2.94 g (0.0375 mol) of acetyl chloride was added drop-wise into a flask containing 5 g (0.0125 mol) N,N"-2-hydroxyl-1,3-propanediylbis(N'-octyl)urea above intermediate in 33.3 g of 1M LiCl/NMP. The flask was held at about 10° C. during the addition. The flask was equipped with a stirrer. The reaction mixture was allowed to warm to room temperature and stirred for overnight. The reaction mixture was monitored with a NMR spectrometer and when the chemical shift (CH—) corresponded to the desired structure and the integration was correct, the reaction was considered completed. The product was precipitated by water, collected by filtration and subsequently drying under vacuum to give a white powder (2.55 g, 46.1% yield). The resulting rheology control agent had the following formula:

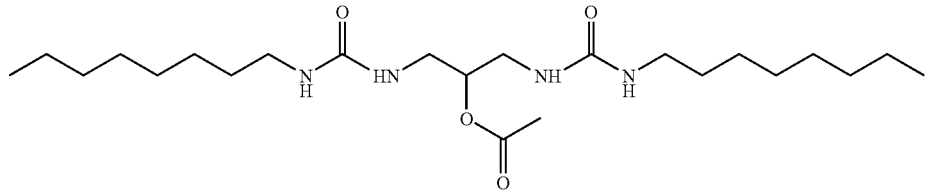

Example 11

The reaction was carried out under a blanket of nitrogen. 4.52 g (0.0375 mol) of valeryl chloride was added drop-wise into a flask containing 5 g (0.0125 mol) N,N"-2-hydroxyl-1,3-propanediylbis(N'-octyl)urea in 33.3 g of 1M LiCl/NMP. The flask was held at about 10° C. during the addition. The flask was equipped with a stirrer. The reaction mixture was allowed to warm to room temperature and stirred for overnight. The reaction mixture was monitored with a NMR spectrometer and when the chemical shift (CH—) corresponded to the desired structure and the integration was correct, the reaction was considered completed. The product was precipitated by water, collected by filtration and subsequently drying under vacuum to give a white powder (3.11 g, 51.3% yield). The resulting rheology control agent had the following formula:

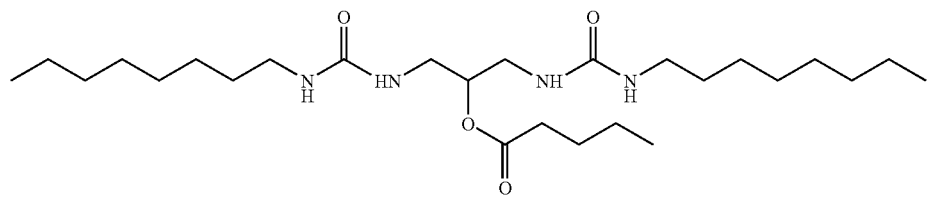

Example 12

The following reaction was carried out under a blanket of nitrogen. 4.77 g (31.0 mmol) of octylisocyanate in 20 mL of chloroform was added dropwise into a flask containing 3.75 g (15.5 mmol) lysine ethylester hydrochloride and 3.49 g (35.0 mmol) triethylamine in 80 mL of chloroform. The flask was held at about 10° C. during the addition. The flask was equipped with a stirrer. The reaction mixture was monitored with an IR spectrophotometer and when the isocyanate peak (about 2258 cm$^{-1}$) disappeared the reaction was considered completed. The reaction mixture was allowed to warm to room temperature and stirred for overnight. The product was collected by filtration and subsequently drying under vacuum to give a white powder (6.2 g, 86.1% yield). The resulting rheology control agent had the following formula:

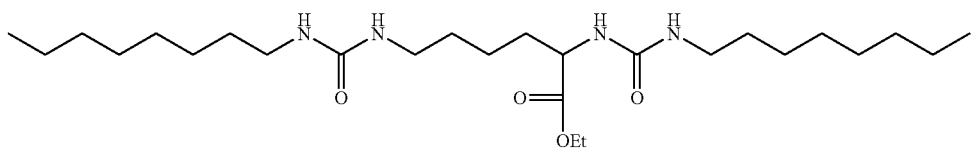

Example 13

The following reaction was carried out under a blanket of nitrogen. An organic isocyanate of 3.27 g (0.020 mol) of octyl isocyanate was added drop-wise into a flask equipped with a stirrer containing 3.175 g (0.020 mol) of L-serine methyl ester hydrochloride and 3.04 g (0.030 mol) of triethylamine in 100 mL acetonitrile. The flask was held at about 10° C. during the addition. The flask was equipped with a stirrer. The reaction mixture was allowed to warm to room temperature and stirred for 2 hours. The reaction mixture was monitored with an LC/MS. When the corresponding peaks of the starting materials disappeared and the spectrum showed the expected intermediate mass peak of methyl 3-hydroxy-2-(3-octylureido)propanoate, the reaction was considered completed. In the same reaction flask, 0.08 g of dibutyltindilaurate and 1.68 g (0.010 mol) of 1,6-diisocyanatohexane were added. The reaction mixture was refluxed at 78° C. for about 2 hours with constant stirring. The reaction mixture was monitored with an LC/MS. When the corresponding peaks of the starting materials disappeared and the spectrum showed the expected mass peak of final product, the reaction was considered completed. The reaction mixture was filtered and washed with water to remove the product formed and any residual solvent was removed under vacuum to give a white powder (5.16 g, 77.0% yield). The resulting rheology control agent had the following formula:

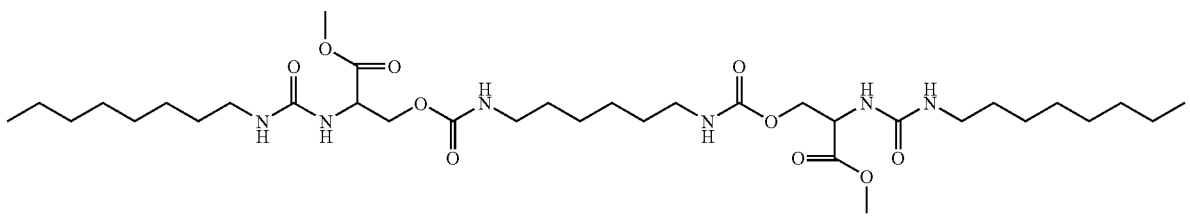

Example 14

The following reaction was carried out under a blanket of nitrogen. An organic isocyanate of 3.27 g (0.020 mol) of octyl isocyanate was added drop-wise into a flask equipped with a stirrer containing 3.175 g (0.020 mol) of L-serine methyl ester hydrochloride and 3.04 g (0.030 mol) of triethylamine in 100 mL acetonitrile. The flask was held at about 10° C. during the addition. The flask was equipped with a stirrer. The reaction mixture was allowed to warm to room temperature and stirred for 2 hours. The reaction mixture was monitored with an LC/MS. When the corresponding peaks of the starting materials disappeared and the spectrum showed the expected intermediate mass peak of methyl 3-hydroxy-2-(3-octylureido)propanoate, the reaction was considered completed. In the same reaction flask, 0.08 g of dibutyltindilaurate and 2.61 g (0.020 mol) of cyclohexylisocynate were added. The reaction mixture was refluxed at 78° C. for about 2 hours with constant stirring. The reaction mixture was monitored with an LC/MS. When the corresponding peaks of the starting materials disappeared and the spectrum showed the expected mass peak of final product, the reaction was considered complete. The reaction mixture was filtered and washed with water to obtain the product and any residual solvent was removed under vacuum to give a white powder (5.80 g, 72.5% yield). The resulting rheology control agent had the following formula:

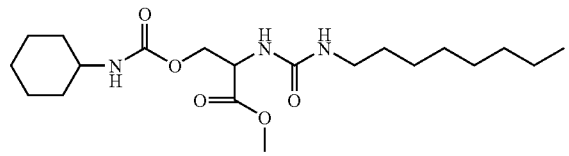

Example 15

The following reaction was carried out under a blanket of nitrogen. An organic isocyanate of 2.71 g (0.021 mol) of cyclohexyl isocyanate was added drop-wise into a flask equipped with a stirrer containing 3.24 g (0.021 mol) of L-serine methyl ester hydrochloride and 4.21 g (0.042 mol) of triethylamine in 100 mL acetonitrile. The flask was held at about 10° C. during the addition. The flask was equipped with a stirrer. The reaction mixture was allowed to warm to room temperature and stirred for 2 hours. The reaction mixture was monitored with an LC/MS. When the corresponding peaks of the starting materials disappeared and the spectrum showed the expected intermediate mass peak of methyl 2-(3-cyclohexylureido)-3-hydroxypropanoate, the reaction was considered completed. In the same reaction flask, 0.08 g of dibutyltindilaurate and 3.40 g (0.021 mol) of octylisocyanate were added. The reaction mixture was refluxed at 78° C. for about 2 hours with constant stirring. The reaction mixture was monitored with an LC/MS. When the corresponding peaks of the starting materials disappeared and the spectrum showed the expected mass peak of final product, the reaction was considered completed and the reaction mixture was filtered and washed with water to obtain the product and any residual solvent was removed under vacuum to give a white powder (3.59 g, 43.5% yield). The resulting rheology control agent had the following formula:

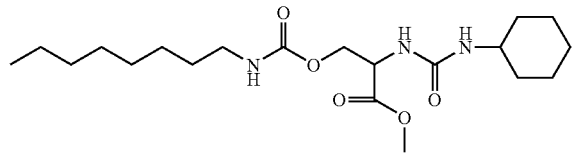

Example 16

An acrylic or polyester based coating resin was combined with 2% of the rheology control agent and diluted with appropriate amount of solvent. After through mixing, the mixture was aged for at least one hour before viscosity was measured. The results on various rheology control agents are shown in Table 1.

TABLE 1

| Rheology Agent | Resin | Solid wt % Rheology agent | Viscosity Cps 0.5 rpm | Viscosity Cps 5 rpm | Viscosity cps 50 rpm | Viscosity cps 100 rpm | Viscosity cps 250 rpm |
|---|---|---|---|---|---|---|---|
| Example 1 | High Tg Acrylic Resin | 2 | 28200 | 4560 | 668 | 496 | 416 |
| Example 3 | High Tg Acrylic Resin | 2 | 6400 | 1580 | 446 | 345 | 262 |
| Example 6 | High Tg Acrylic Resin | 2 | 2000 | 560 | 264 | 232 | 198 |
| Example 8 | High Tg Acrylic Resin | 2 | 28400 | 2240 | 616 | 497 | 409 |
| Example 3 | Low Mw Polyester | 2 | 44600 | 2000 | 720 | 553 | 358 |
| Example 6 | Low Mw Polyester | 2 | 10600 | 2100 | 392 | 260 | 170 |
| Example 8 | Low Mw Polyester | 2 | 11200 | 1440 | 340 | 270 | 236 |
| Control | Low Mw Polyester | 0 | 60 | 60 | 68 | 65 | 63 |

*High Tg Acrylic Resin- 58% solids in organic solvents of an acrylic polymer of S/MMA/IBMA/HEMA having a Mn of 6200 and Mw 12,000 and prepared according to Example (Col. 5) U.S. Pat. No. 5,279,862.
*Low Mw Polyester is prepared according to the teachings in WO 2003/070843
S—styrene,
MMA—methyl methacrylate,
IBMA—isobutylmethacrylate,
HEMA—2-hydroxy ethyl methacrylate.

Example 17

| Dispersion preparation | #1 | #2 |
|---|---|---|
| Add in order with mixing | | |
| Highly Branched Copolyester Polyol* | 58.68 | 58.68 |
| Butyl acetate/Butanol (80/20 weight % blend) | 147.48 | 147.48 |
| Add slowly with mixing at high speed (approximately 5000 RPM) on a lab top high speed disperser using a blade with a diameter of approximately 6 cm. | | |
| Rheology control agent of Example 2 (35% in NMP) | 12.6 | 16.8 |
| Mix at high speed (approximately 5000 RPM) on a lab top high speed disperser, using a blade with a diameter of approximately 6 cm. for 30 minutes. | | |
| Add with low speed mixing | | |
| Butyl acetate/Butanol (80/20 weight % blend) | 25.0 | 25.0 |

*Same composition as Solution 5 of WO 03/070843 but made in methyl amyl ketone as the solvent vs. propylene glycol monomethyl ether acetate.

Basecoat Preparation

| Solvent Blend A | |
|---|---|
| Component | Grams |
| Acetone | 162 |
| Isobutyl alcohol | 234 |
| Isopropanol | 180 |
| Methyl Isobutyl Ketone | 108 |
| Aliphatic hydrocarbon (bp = 90-110 C.) | 270 |
| Xylene | 216 |
| Aromatic hydrocarbon (bp = 150-190 C.) | 18 |
| Total | 1188 |

| Solvent Blend B | |
|---|---|
| Component | Grams |
| Butyl acetate | 7964.60 |
| Methyl amyl ketone | 3413.40 |
| Total | 11378.00 |

A CAB Solution, shown below, was produced by slowly adding cellulose acetate butyrate to solvent while mixing on an air mixer:

| Component | Description | Grams |
|---|---|---|
| Solvent Blend B | Solvent Blend | 5055.57 |
| CAB-381-2* | cellulose acetate butyrate | 669.12 |
| CAB-531-1* | cellulose acetate butyrate | 223.04 |
| | Total | 5947.73 |

*Supplied by Eastman Chemical Co., Kingsport, Tennessee.

| Silver Metallic Tinting Composition | |
|---|---|
| Acrylic resin * | 46.02 |
| Sparkle Silver 5745 Aluminum Paste from Silberline | 25.47 |
| Solvent Blend A | 24.91 |

* A random acrylic copolymer Sty/IBOMA/EHA/HEMA/BMA/MMA (10/10/15/30/10/25% by weight) at 66.40% wt solids in n-butyl acetate was prepared with the standard free radical polymerization procedure.

Basecoat lacquer coating composition (Exhibit 1 & Exhibit 2) were made by adding the components listed in Table 2 in order on an air mixer:

TABLE 2

| Component | Coating Exhibit 1 | Coating Exhibit 2 |
|---|---|---|
| Dispersion preparation #1 | 246.76 | |
| Dispersion preparation #2 | | 247.96 |
| Graft acrylic copolymer prepared in accordance with the procedure described in Example #6 of U.S. Pat. No. 6,472,463 but using methyl toluene sulfonate versus benzyl chloride | 2.82 | 2.82 |
| Acrylic resin * | 9.2 | 9.2 |
| Graft copolymer (Example #1 of U.S. Ser. No. 10/983,462) | 79.7 | 79.7 |
| CAB solution (prepared above) | 152.78 | 152.78 |
| Silver Metallic tinting composition | 96.4 | 96.4 |
| Solvent blend A | 219.55 | 219.55 |

* A random acrylic copolymer Sty/IBOMA/EHA/HEMA/BMA/MMA (10/10/15/30/10/25% by weight) at 66.40% wt solids in n-butyl acetate was prepared with the standard free radical polymerization procedure.
BMA—butyl methacrylate, IBOMA—isobornyl methacrylate.

Panel Preparation

The silver basecoats were sprayed per the application instructions used for DuPont™ ChromaPremier® Basecoat specified in the DuPont ChromaSystem Tech Manual. The basecoats were sprayed to hiding over ACT APR10288 cold rolled steel panels which were wiped with DuPont First Klean 3900S™, sanded with 80 grit sand paper, wiped again with DuPont First Klean 3900S™, then primed with DuPont™ Variprime® 615S™/625S™ Self-Etching Primer as per the instructions in the DuPont ChromaSystem Tech Manual. The basecoats were clearcoated with DuPont™ ChromaClear® V-7500S™ Multi-Use as per the instructions in the DuPont ChromaSystem Tech Manual. Basecoat/clearcoat panels were flashed and then baked in a 140° F. (60° C.) oven for 30 minutes. Topcoated panels were allowed to air dry for an additional 7 days prior to testing.

Below in Table 3 are tabulated, the Head-Brightness (HOB) and flop values for these coatings. Measurements were taken with a DuPont ChromaVision Custom Color MA 100B meter manufactured by X-Rite, Inc. of Grandville, Mich.

TABLE 3

| Basecoat | Near spec Lightness:HOB | Flop |
|---|---|---|
| Exhibit 1 | 118.67 | 5.93 |
| Exhibit 2 | 132.96 | 8.39 |

This data shows that the use of the rheology control agent of this invention gave exception flake control in a refinish lacquer basecoat. This is even more remarkable in coating Exhibit 2 (with an HOB of 132.96), which uses 4% on binder of the rheology control agent. This level of rheology control agent is much lower than the typical level of traditional rheology control agents such as wax, which are used at around 10% on binder in these types of coatings. Thus the rheology control agents of this invention give excellent coating appearance at much lower levels than traditional rheology control agents.

Example 18

The above prepared rheology control agents of Examples 2, 4, 8, 9 and 14 were tested for rheological activity in a waterborne based coating composition, Aquacryl® 514, described in U.S. Pat. No. 6,204,319. Each of the waterborne coating compositions was blended with 5% of various rheology control agents and diluted with an appropriate amount of aqueous carrier. After mixing vigorously, the mixture was checked for gelation/viscosity increase after certain times by inverting the container.

The results on various rheology control agents are shown in following Table 4:

TABLE 4

| Rheology Control Agents | RCA Solid wt % | Gel time (hh:mm:ss) |
| --- | --- | --- |
| Ex. 2 | 5 | 3:00:00 |
| Ex. 4 | 5 | 12:00:00 |
| Ex. 8 | 5 | Viscous |
| Ex. 9 | 5 | 00:10:00 |
| Ex. 14 | 5 | 12:00:00 |

The above test results shown in Table 4 show that 5 wt % of the rheology control agent of this invention thickens a water borne coating composition effectively. Gel activity depends on the structure of a rheology control agent and the resin used in the aqueous coating composition.

What is claimed is:

1. A coating composition comprising a rheology control agent having a formula selected from the group consisting of

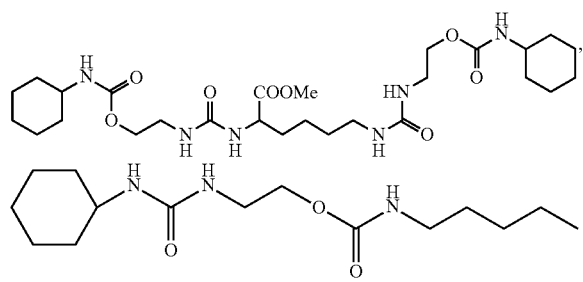

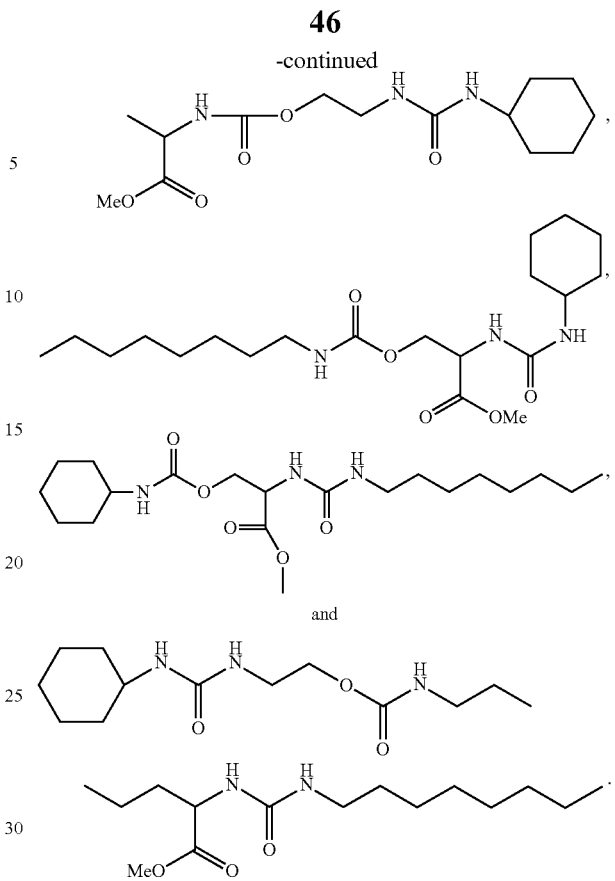

and

2. The coating composition of claim 1 wherein the coating composition is a solventborne coating composition or a waterborne coating composition.

3. The coating composition of claim 1 wherein the coating composition is a clear coat composition, basecoat composition, pigmented mono coating composition, primer surfacer composition or a primer filler composition.

4. The coating composition of claim 1 wherein the coating composition containing a binder, wherein the binder is selected from the group consisting of polyacrylates, linear poly(meth)acrylates, branched, graft or segmented poly(meth)acrylates, acrylic alkyd resins, polyesters, branched copolyesters, carbamate functional polymers, polyepoxides, oligomers and polyesterurethanes.

5. The coating composition of claim 4 wherein the coating composition further comprises a crosslinking agent selected from the group consisting of polyisocyanates, blocked polyisocyanates, alkylated melamines, melamine derivatives, benzoguanamines, silanes and epoxides.

* * * * *

UNITED STATES PATENT AND TRADEMARK OFFICE
CERTIFICATE OF CORRECTION

PATENT NO. : 8,030,513 B2  
APPLICATION NO. : 12/758864  
DATED : October 4, 2011  
INVENTOR(S) : Christian Peter Lenges et al.

Page 1 of 1

It is certified that error appears in the above-identified patent and that said Letters Patent is hereby corrected as shown below:

On the Title Page

Please add the following section to the first page of the patent:

Item --(60) Related application data--
--Division of U.S. Patent Application No. 11/330,436, now U.S. Patent 7,741,510, filed January 12, 2006, non-provisional of Provisional Application No. 60/643,482, filed January 13, 2005.--

Signed and Sealed this
Twenty-fifth Day of February, 2014

Michelle K. Lee
*Deputy Director of the United States Patent and Trademark Office*